United States Patent
Bardy

(10) Patent No.: US 8,231,539 B2
(45) Date of Patent: Jul. 31, 2012

(54) AUTOMATED PATIENT CARE SYSTEM AND METHOD FOR DIAGNOSING AND MONITORING RESPIRATORY INSUFFICIENCY

(75) Inventor: Gust H. Bardy, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1372 days.

(21) Appl. No.: 11/879,654

(22) Filed: Jul. 17, 2007

(65) Prior Publication Data
US 2007/0265542 A1 Nov. 15, 2007

Related U.S. Application Data

(60) Division of application No. 10/646,243, filed on Aug. 22, 2003, now Pat. No. 7,258,670, which is a continuation of application No. 10/152,207, filed on May 20, 2002, now Pat. No. 7,207,945, which is a continuation of application No. 09/442,125, filed on Nov. 16, 1999, now Pat. No. 6,398,728.

(51) Int. Cl.
*A61B 5/08* (2006.01)
*A61B 5/04* (2006.01)
*A61B 5/02* (2006.01)

(52) U.S. Cl. ........ 600/529; 600/484; 600/532; 600/538; 600/513; 600/485; 600/536; 128/920; 128/923

(58) Field of Classification Search .......... 600/529–543, 600/484; 128/920–925
See application file for complete search history.

(56) References Cited

U.S. PATENT DOCUMENTS

| | | | |
|---|---|---|---|
| 3,832,339 | A | 8/1974 | Aisenberg et al. |
| 4,142,533 | A | 3/1979 | Brownlee et al. |
| 4,197,856 | A | 4/1980 | Northrop |
| 4,531,527 | A | 7/1985 | Reinhold, Jr. et al. |

(Continued)

FOREIGN PATENT DOCUMENTS
EP 0 342 859 11/1989
(Continued)

OTHER PUBLICATIONS

File history (as of Oct. 5, 2010) for co-pending U.S. Appl. No. 11/789,388, filed Apr. 23, 2007, entitled "System and Method for Determining Edema Through Remote Patient Monitoring", which claims priority to the same parent application (U.S. Appl. No. 09/442,125, now U.S. Pat. No. 6,398,728) (184 pages).

(Continued)

*Primary Examiner* — Navin Natnithithadha
(74) *Attorney, Agent, or Firm* — Pauly, DeVries Smith & Deffner LLC

(57) ABSTRACT

An automated patient care system and method for diagnosing and monitoring respiratory insufficiency is presented. A plurality of monitoring sets are stored into a database. Each monitoring set includes recorded measures, which each relate to patient information and contain medical device measures recorded on a substantially continuous basis or derived measures calculable therefrom. The monitoring sets are retrieved from the database. A set of indicator thresholds are defined. Each indicator threshold corresponds to a quantifiable physiological measure of a pathophysiology indicative of respiratory insufficiency. A respiratory insufficiency finding is diagnosed. A change in patient status is determined by comparing at least one recorded measure to at least one other recorded measure with both recorded measures relating to the same type of patient information. Each patient status change is compared to the indicator threshold corresponding to the same type of patient information as the recorded measures.

32 Claims, 28 Drawing Sheets

U.S. PATENT DOCUMENTS

| | | |
|---|---|---|
| 4,686,999 A | 8/1987 | Snyder et al. |
| 4,803,625 A | 2/1989 | Fu et al. |
| 4,809,697 A | 3/1989 | Causey, III et al. |
| 4,852,570 A | 8/1989 | Levine |
| 4,899,758 A | 2/1990 | Finkelstein et al. |
| 4,958,645 A | 9/1990 | Cadell et al. |
| 4,974,607 A | 12/1990 | Miwa |
| 4,987,897 A | 1/1991 | Funke |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| 5,199,428 A | 4/1993 | Obel et al. |
| 5,301,105 A | 4/1994 | Cummings, Jr. |
| 5,309,919 A | 5/1994 | Snell et al. |
| 5,313,593 A | 5/1994 | Barakat et al. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,606,976 A | 3/1997 | Marshall et al. |
| 5,660,183 A | 8/1997 | Chiang et al. |
| 5,673,691 A | 10/1997 | Abrams et al. |
| 5,687,734 A | 11/1997 | Dempsey et al. |
| 5,697,959 A | 12/1997 | Poore |
| 5,704,345 A | 1/1998 | Berthon-Jones |
| 5,704,366 A | 1/1998 | Tacklind et al. |
| 5,711,297 A | 1/1998 | Iliff |
| 5,713,350 A | 2/1998 | Yokota et al. |
| 5,720,770 A | 2/1998 | Nappholz et al. |
| 5,720,771 A | 2/1998 | Snell |
| 5,724,580 A | 3/1998 | Levi et al. |
| 5,724,968 A | 3/1998 | Iliff |
| 5,724,983 A | 3/1998 | Selker et al. |
| 5,738,102 A | 4/1998 | Lemelson |
| 5,743,267 A | 4/1998 | Nikolic |
| 5,749,907 A | 5/1998 | Mann |
| 5,749,908 A | 5/1998 | Snell |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve |
| 5,941,837 A | 8/1999 | Amano et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun |
| 6,063,028 A | 5/2000 | Luciano |
| 6,067,466 A | 5/2000 | Selker |
| 6,073,046 A | 6/2000 | Patel |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,122,351 A | 9/2000 | Schlueter, Jr. et al. |
| 6,126,595 A | 10/2000 | Amano et al. |
| 6,129,675 A | 10/2000 | Jay |
| 6,135,951 A | 10/2000 | Richardson et al. |
| 6,139,494 A | 10/2000 | Cairnes |
| 6,152,882 A | 11/2000 | Prutch |
| 6,155,267 A | 12/2000 | Nelson |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,190,324 B1 | 2/2001 | Kieval et al. |
| 6,223,078 B1 | 4/2001 | Marcovecchio |
| 6,225,901 B1 | 5/2001 | Kail, IV |
| 6,234,964 B1 | 5/2001 | Iliff |
| 6,246,992 B1 | 6/2001 | Brown |
| 6,249,705 B1 | 6/2001 | Snell |
| 6,250,309 B1 | 6/2001 | Krichen et al. |
| 6,263,245 B1 | 7/2001 | Snell |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker |
| 6,306,088 B1 | 10/2001 | Krausman et al. |
| 6,336,900 B1 | 1/2002 | Alleckson |
| 6,363,282 B1 | 3/2002 | Nichols et al. |
| 6,398,728 B1 | 6/2002 | Bardy |
| 6,409,675 B1 | 6/2002 | Turcott |
| 6,411,840 B1 | 6/2002 | Bardy |
| 6,416,471 B1 | 7/2002 | Kumar et al. |
| 6,428,483 B1 | 8/2002 | Carlebach |
| 6,440,066 B1 | 8/2002 | Bardy |
| 6,442,433 B1 | 8/2002 | Linberg |
| 6,454,705 B1 | 9/2002 | Cosentino |
| 6,477,424 B1 | 11/2002 | Thompson et al. |
| 6,662,032 B1 * | 12/2003 | Gavish et al. ............ 600/323 |
| 6,811,537 B2 | 11/2004 | Bardy |
| 6,827,670 B1 | 12/2004 | Stark et al. |
| 6,834,203 B2 | 12/2004 | Bardy |
| 6,931,272 B2 | 8/2005 | Burnes |
| 6,951,539 B2 | 10/2005 | Bardy |
| 7,117,028 B2 | 10/2006 | Bardy |
| 7,207,945 B2 | 4/2007 | Bardy |
| 7,258,670 B2 | 8/2007 | Bardy |
| 7,387,610 B2 | 6/2008 | Stahmann et al. |
| 7,429,243 B2 | 9/2008 | KenKnight et al. |
| 7,480,528 B2 | 1/2009 | Brockway et al. |
| 7,959,574 B2 | 6/2011 | Bardy |
| 2002/0169367 A1 | 11/2002 | Bardy |
| 2003/0055679 A1 | 3/2003 | Soll et al. |
| 2007/0083241 A1 | 4/2007 | Bardy |
| 2007/0203415 A1 | 8/2007 | Bardy |

FOREIGN PATENT DOCUMENTS

| | | |
|---|---|---|
| EP | 0 513 457 | 11/1992 |
| EP | 0 531 889 A2 | 3/1993 |
| EP | 0 711 531 A1 | 5/1996 |
| WO | WO 97/39792 | 10/1997 |
| WO | WO 98/07142 | 2/1998 |
| WO | WO 98/42103 | 9/1998 |
| WO | WO 99/46718 | 9/1999 |
| WO | WO 99/55226 | 11/1999 |

OTHER PUBLICATIONS

File history for co-pending U.S. Appl. No. 11/789,387, filed Mar. 26, 2007, entitled "System and Method for Managing Respiratory Insufficiency Through Remote Patient Care" which claims priority to the same parent application (U.S. Appl. No. 09/442,125, now U.S. Pat. No. 6,398,728) (213 pages).

File history for co-pending U.S. Appl. No. 11/691,414, filed Mar. 26, 2007, entitled "System and Method for Analyzing a Patient Status for Respiratory Insufficiency for Use in Automated Patient Care" which claims priority to the same parent application (U.S. Appl. No. 09/442,125, now U.S. Pat. No. 6,398,728) (227 pages).

File history for co-pending U.S. Appl. No. 11/894,302, filed Aug. 20, 2007, entitled "System and Method for Managing Respiratory Insufficiency in Conjunction with Heart Failure Assessment", which claims priority to the same parent application (U.S. Appl. No. 09/442,125, now U.S. Pat. No. 6,398,728) (530 pages).

Partial File history (from Aug. 19, 2010 through Mar. 1, 2011) for co-pending U.S. Appl. No. 11/789,387, filed Mar. 26, 2007, entitled "System and Method for Managing Respiratory Insufficiency Through Remote Patient Care" which claims priority to the same parent application (U.S. Appl. No. 09/442,125, now U.S. Pat. No. 6,398,728) as the present application (U.S. Appl. No. 11/894,302) (63 pages).

Partial File history (from Oct. 20, 2010 through Mar. 1, 2011) for co-pending U.S. Appl. No. 11/691,414, filed Mar. 26, 2007, entitled "System and Method for Analyzing a Patient Status for Respiratory Insufficiency for Use in Automated Patient Care" which claims priority to the same parent application (U.S. Appl. No. 09/442,125, now U.S. Pat. No. 6,398,728) as the present application (U.S. Appl. No. 11/894,302) (31 pages).

Moody GB, "Integration of Real-Time and Off-Line Clinical Data in the MIMIC Database," Computers in Cardiology 1997 vol. 24, pp. 585-588, Cambridge, MA USA.

Long WJ, et al., "Differential Diagnosis Generation From a Causal Network With Probabilities," Computers in Cardiology, 1988, Proceedings, pp. 185-188, Washington DC, USA.

Dunn et al., "Telemedicine Links Patients in Sioux Lookout with Doctors in Toronto," CMA Journal, vol. 122, pp. 484-487 (Feb. 23, 1980).

Auer et al., "Paced Epimyocardial Electrograms for Noninvasive Rejection Monitoring After Heart Transplantation," The Journal of Heart and Lung Transplantation, vol. 15, No. 10, pp. 993-998 (Oct. 1996).

Schreier et al., "A Non-Invasive Rejection Monitoring System Based on Remote Analysis of Intramyocardial Electrograms from Heart Transplants," IEEE, pp. 35-36 (1997).

Roberge et al., "Basic and Applied Biomedical Engineering Building Blocks for Health Care," 1995 IEEE Engineering in Medicine and Biology 17$^{th}$ Annual Conference, vol. 1, Montreal-Canada, (Sep. 20-23, 1995).

Hutten et al., "Cardiac Telemonitoring by Integrating Pacemaker Telemetry within Worldwide Data Communication Systems," Proceedings of 19$^{th}$ International Conference, IEEE/EMBS, Chicago, IL, pp. 974-976 (Oct. 30-Nov. 2, 1997).

Vargas, Juan E., "Home-Based Monitoring of Cardiac Patients," Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Magrabi et al., "Web Based Longitudinal ECG Monitoring," Proceedings of 20$^{th}$ Annual International Conference of the IEEE Engineering in Medicine and Biology Society, vol. 20, No. 3, pp. 1155-1158 (1998).

Nelwan et al., "Ubiquitous Access to Real-Time Patient Monitoring Data," Computers in Cardiology., vol. 24, pp. 271-274 (1997).

"Non Final Office Action Received", mailed Nov. 23, 2011 in co-pending, co-owned U.S. Appl. No. 11/894,302, "System and Method for Managing Respiratory Insufficiency in Conjunction with Heart Failure Assessment," (26 pages).

"Response to Non-Final Office Action", mailed Nov. 23, 2011 in co-pending, co-owened U.S. Appl. No. 11/894,302, "System and Method for Managing Respiratory Insufficiency in Conjunction with Heart Failure Assessment," filed with USPTO Feb. 23, 2012, (11 pages).

* cited by examiner

Fig. 6.

Patient 1

| Set 0 | | | | Set n-2 | Set n-1 | Set n |
|---|---|---|---|---|---|---|
| $X_0$ | • | • | • | $X_{n-2}$ | $X_{n-1}$ | $X_n$ |
| $Y_0$ | • | • | • | $Y_{n-2}$ | $Y_{n-1}$ | $Y_n$ |
| $Z_0$ | • | • | • | $Z_{n-2}$ | $Z_{n-1}$ | $Z_n$ | time →

Patient 2

| Set 0 | | | | Set n-2 | Set n-1 | Set n |
|---|---|---|---|---|---|---|
| $X_{0'}$ | • | • | • | $X_{n-2'}$ | $X_{n-1'}$ | $X_{n'}$ |
| $Y_{0'}$ | • | • | • | $Y_{n-2'}$ | $Y_{n-1'}$ | $Y_{n'}$ |
| $Z_{0'}$ | • | • | • | $Z_{n-2'}$ | $Z_{n-1'}$ | $Z_{n'}$ | time →

Patient 3

| Set 0 | | | | Set n-2 | Set n-1 | Set n |
|---|---|---|---|---|---|---|
| $X_{0''}$ | • | • | • | $X_{n-2''}$ | $X_{n-1''}$ | $X_{n''}$ |
| $Y_{0''}$ | • | • | • | $Y_{n-2''}$ | $Y_{n-1''}$ | $Y_{n''}$ |
| $Z_{0''}$ | • | • | • | $Z_{n-2''}$ | $Z_{n-1''}$ | $Z_{n''}$ | time →

AUTOMATED PATIENT CARE SYSTEM AND METHOD FOR DIAGNOSING AND MONITORING RESPIRATORY INSUFFICIENCY

CROSS-REFERENCE TO RELATED APPLICATION

This patent application is a divisional of application Ser. No. 10/646,243, filed Aug. 22, 2003, now U.S. Pat. No. 7,258,670, issued Aug. 21, 2007; which is a continuation of application Ser. No. 10/152,207, filed May 20, 2002, now U.S. Pat. No. 7,207,945, issued Apr. 24, 2007; which is a continuation of application Ser. No. 09/442,125, filed Nov. 16, 1999, now U.S. Pat. No. 6,398,728, issued Jun. 4, 2002, the disclosures of which are incorporated by reference.

FIELD

The present invention relates in general to respiratory insufficiency diagnosis and analysis, and, in particular, to an automated patient care system and method for diagnosing and monitoring respiratory insufficiency throughout disease onset, progression, regression, and status quo.

BACKGROUND

Presently, respiratory insufficiency due to primary diseases of the lungs is one of the leading causes of acute and chronic illness in the world. Clinically, respiratory insufficiency involves either difficulty in ventilation or in oxygenation. The former is manifest by increases in the arterial partial pressure of carbon dioxide and the latter is manifest by decreases in arterial partial pressure of oxygen. For purposes of this invention, the term "respiratory insufficiency" will refer to ventilatory insufficiency and/or to problems in oxygenation due to diseases of the lung. Common causes of respiratory insufficiency include bronchitis, emphysema, pneumonia, pulmonary emboli, congestive heart failure, tumor infiltration of the lung and abnormalities of the interstitium of the lungs that may be infectious in origin, due to immunological abnormalities, or as a result of exposure to environmental pathogens. The effects of respiratory insufficiency range from cough to impairment during physical exertion to a complete failure of lung function and respiratory arrest at any level of activity. Clinical manifestations of respiratory insufficiency include respiratory distress, such as shortness of breath and fatigue, cough, and reduced exercise capacity or tolerance.

Several factors make the early diagnosis and prevention of respiratory insufficiency, as well as the monitoring of the progression of respiratory insufficiency, relatively difficult. First, the onset of respiratory insufficiency is generally subtle and erratic. Often, the symptoms are ignored and the patient compensates by changing his or her daily activities. This situation is especially true in chronic lung disorders where the onset of symptoms can be very gradual. As a result, many respiratory insufficiency conditions or deteriorations in respiratory insufficiency remain undiagnosed until more serious problems arise seriously limiting the activities of daily living.

The susceptibility to suffer from respiratory insufficiency depends upon the patient's age, sex, physical condition, and other factors, such as smoking history, occupation, diabetes, co-existing heart disease, immunodepression, the presence or absence of cancer, surgical history, kidney function, and extent of pre-existing lung disease. No one factor is dispositive. Finally, annual or even monthly lung checkups, including chest X-rays or other lung tests, provide, at best, a "snapshot" of patient wellness and the incremental and subtle clinicophysiological changes which portend the onset or progression of respiratory insufficiency often go unnoticed, even with regular health care. Documentation of subtle improvements following therapy that can guide and refine further evaluation and therapy can be equally elusive.

Nevertheless, taking advantage of frequently and regularly measured physiological measures, such as recorded manually by a patient, via an external monitoring or therapeutic device, or via implantable device technologies, can provide a degree of detection and prevention heretofore unknown. For instance, patients already suffering from some form of treatable heart disease often receive an implantable pulse generator (IPG), cardiovascular or heart failure monitor, therapeutic device, or similar external wearable device, with which rhythm and structural problems of the heart can be monitored and treated. These types of devices, although usually originally intended for use in treating some type of cardiac problem, can contain sufficient physiological data to allow accurate assessment of lung disorders. Such devices are useful for detecting physiological changes in patient conditions through the retrieval and analysis of telemetered signals stored in an on-board, volatile memory. Typically, these devices can store more than thirty minutes of per heartbeat and respiratory cycle data recorded on a per heartbeat, per respiration, binned average basis, or on a derived basis from, for example, atrial or ventricular electrical activity, minute ventilation, patient activity score, cardiac output score, arterial or mixed venous oxygen score, cardiopulmonary pressure measures, and the like. However, the proper analysis of retrieved telemetered signals requires detailed medical subspecialty knowledge, particularly by pulmonologists and cardiologists.

Alternatively, these telemetered signals can be remotely collected and analyzed using an automated patient care system. One such system is described in a related, commonly assigned U.S. Pat. No. 6,312,378, issued Nov. 6, 2001, the disclosure of which is incorporated herein by reference. A medical device adapted to be implanted in an individual patient records telemetered signals that are then retrieved on a regular, periodic basis using an interrogator or similar interfacing device. The telemetered signals are downloaded via an internetwork onto a network server on a regular, e.g., daily, basis and stored as sets of collected measures in a database along with other patient care records. The information is then analyzed in an automated fashion and feedback, which includes a patient status indicator, is provided to the patient.

While such an automated system can serve as a valuable tool in providing remote patient care, an approach to systematically correlating and analyzing the raw collected telemetered signals, as well as manually collected physiological measures, through applied pulmonary and cardiovascular medical knowledge to accurately diagnose the onset of a particular medical condition, such as respiratory insufficiency, is needed, especially in patients with co-existing heart disease. One automated patient care system directed to a patient-specific monitoring function is described in U.S. Pat. No. 5,113,869 ('869) to Nappholz et al. The '869 patent discloses an implantable, programmable electrocardiography (ECG) patient monitoring device that senses and analyzes ECG signals to detect ECG and physiological signal characteristics predictive of malignant cardiac arrhythmias. The monitoring device can communicate a warning signal to an external device when arrhythmias are predicted. However, the Nappholz device is limited to detecting tachycardias. Unlike requirements for automated respiratory insufficiency monitoring, the Nappholz device focuses on rudimentary ECG signals indicative of malignant cardiac tachycardias, an already well established technique that can be readily used with on-board signal detection techniques. Also, the Nappholz device is patient specific only and is unable to automatically take into consideration a broader patient or peer group history for reference to detect and consider the progression or improvement of lung disease. Moreover, the Nappholz device has a limited capability to automatically self-reference multiple data points in time and cannot detect disease regression even in the individual patient. Also, the Nappholz device must be implanted and cannot function as an external monitor. Finally, the Nappholz device is incapable of tracking the cardiovascular and cardiopulmonary consequences of any rhythm disorder.

Consequently, there is a need for a systematic approach to detecting trends in regularly collected physiological data indicative of the onset, progression, regression, or status quo of respiratory insufficiency diagnosed and monitored using an automated, remote patient care system. The physiological data could be telemetered signals data recorded either by an external or an implantable medical device or, alternatively, individual measures collected through manual means. Preferably, such an approach would be capable of diagnosing both acute and chronic respiratory insufficiency conditions, as well as the symptoms of other lung disorders. In addition, findings from individual, peer group, and general population patient care records could be integrated into continuous, on-going monitoring and analysis.

SUMMARY

The present invention provides a system and method for diagnosing and monitoring the onset, progression, regression, and status quo of respiratory insufficiency using an automated collection and analysis patient care system. Measures of patient cardiopulmonary information are either recorded by an external or implantable medical device, such as an IPG, cardiovascular or heart failure monitor, or respiratory diagnostic or therapeutic device, or manually through conventional patient-operable means. The measures are collected on a regular, periodic basis for storage in a database along with other patient care records. Derived measures are developed from the stored measures. Select stored and derived measures are analyzed and changes in patient condition are logged. The logged changes are compared to quantified indicator thresholds to detect findings of respiratory distress or reduced exercise capacity indicative of the principal pathophysiological manifestations of respiratory insufficiency: elevated partial pressure of arterial carbon dioxide and reduced partial pressure of arterial oxygen.

An embodiment of the present invention is an automated system and method for diagnosing and monitoring respiratory insufficiency and outcomes thereof. A plurality of monitoring sets is retrieved from a database. Each of the monitoring sets include recorded measures relating to patient information recorded on a substantially continuous basis. A patient status change is determined by comparing at least one recorded measure from each of the monitoring sets to at least one other recorded measure. Both recorded measures relate to the same type of patient information. Each patient status change is tested against an indicator threshold corresponding to the same type of patient information as the recorded measures that were compared. The indicator threshold corresponds to a quantifiable physiological measure of a pathophysiology indicative of respiratory insufficiency.

A further embodiment is an automated collection and analysis patient care system and method for diagnosing and monitoring respiratory insufficiency and outcomes thereof. A plurality of monitoring sets is retrieved from a database. Each monitoring set includes recorded measures that each relate to patient information and include either medical device measures or derived measures calculable therefrom. The medical device measures are recorded on a substantially continuous basis. A set of indicator thresholds is defined. Each indicator threshold corresponds to a quantifiable physiological measure of a pathophysiology indicative of respiratory insufficiency and relates to the same type of patient information as at least one of the recorded measures. A respiratory insufficiency finding is diagnosed. A change in patient status is determined by comparing at least one recorded measure to at least one other recorded measure with both recorded measures relating to the same type of patient information. Each patient status change is compared to the indicator threshold corresponding to the same type of patient information as the recorded measures that were compared.

A further embodiment is an automated patient care system and method for diagnosing and monitoring respiratory insufficiency and outcomes thereof. Recorded measures organized into a monitoring set for an individual patient are stored into a database. Each recorded measure is recorded on a substantially continuous basis and relates to at least one aspect of monitoring reduced exercise capacity and/or respiratory distress. A plurality of the monitoring sets is periodically retrieved from the database. At least one measure related to respiratory insufficiency onset, progression, regression, and status quo is evaluated. A patient status change is determined by comparing at least one recorded measure from each of the monitoring sets to at least one other recorded measure with both recorded measures relating to the same type of patient information. Each patient status change is tested against an indicator threshold corresponding to the same type of patient information as the recorded measures that were compared. The indicator threshold corresponds to a quantifiable physiological measure of a pathophysiology indicative of reduced exercise capacity and/or respiratory distress.

The present invention provides a capability to detect and track subtle trends and incremental changes in recorded patient cardiopulmonary information for diagnosing and monitoring respiratory insufficiency. When coupled with an enrollment in a remote patient monitoring service having the capability to remotely and continuously collect and analyze external or implantable medical device measures, respiratory insufficiency detection, prevention and tracking regression from therapeutic maneuvers become feasible.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 6 is a record view showing, by way of example, a set of partial patient care records for care of patients with respiratory insufficiency stored in the database of the system of FIG. 1;

DETAILED DESCRIPTION

Figure 1:
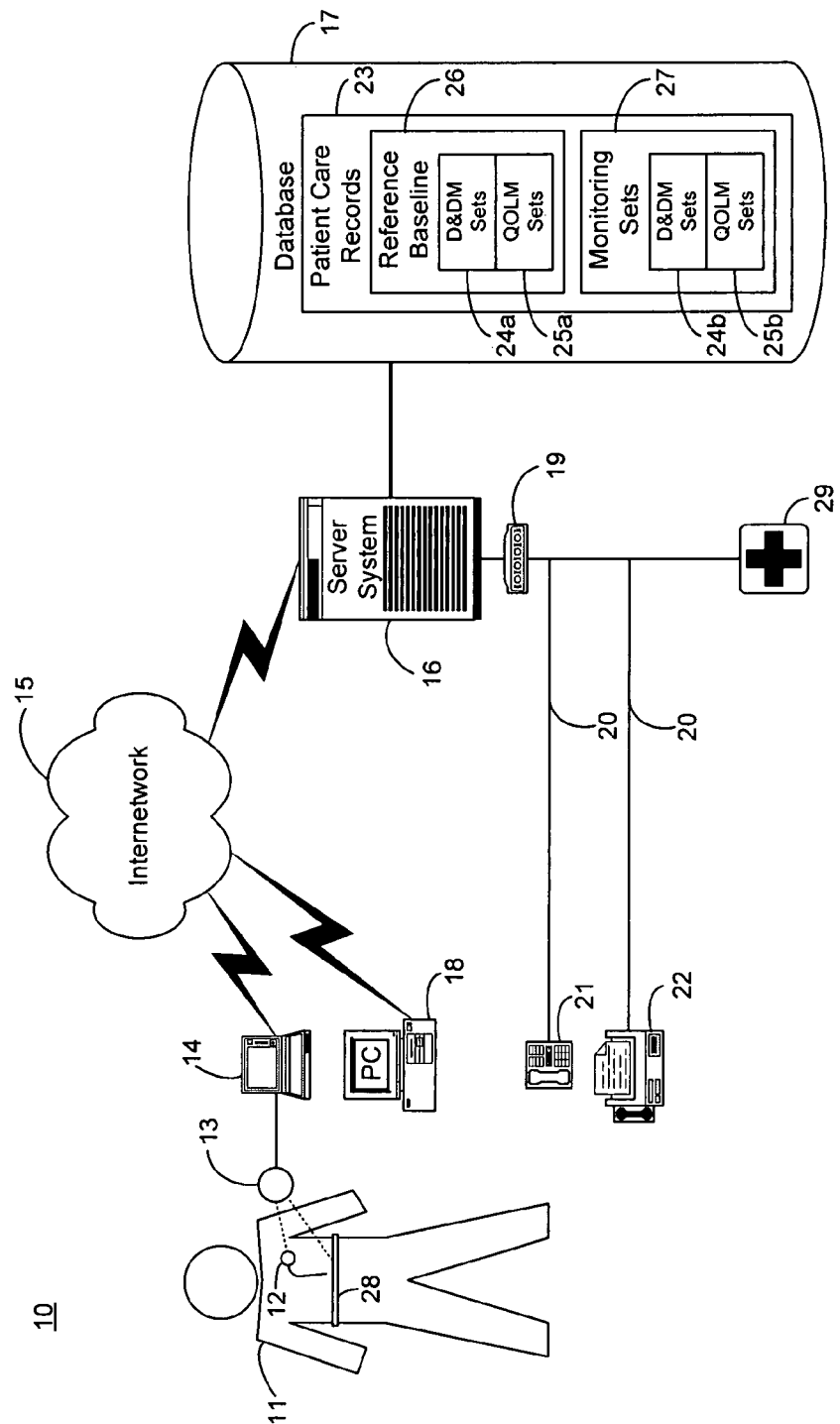
FIG. 1 is a block diagram showing an automated patient care system for diagnosing and monitoring respiratory insufficiency in accordance with the present invention.

FIG. 1 is a block diagram showing an automated collection and analysis patient care system 10 for diagnosing and monitoring respiratory insufficiency in accordance with the present invention. An exemplary automated collection and analysis patient care system suitable for use with the present invention is disclosed in the related, commonly assigned U.S. Pat. No. 6,312,378, issued Nov. 6, 2001, the disclosure of which is incorporated herein by reference. Preferably, an individual patient 11 is a recipient of an implantable medical device 12, such as, by way of example, an IPG, cardiovascular, heart failure monitor, pulmonary monitor, or therapeutic device, with a set of leads extending into his or her heart and electrodes implanted throughout the cardiopulmonary system. Alternatively, an external monitoring or therapeutic medical device 26, a subcutaneous monitor or device inserted into other organs, a cutaneous monitor, or even a manual physiological measurement device, such as an respiratory monitor, electrocardiogram or heart rate monitor, could be used. The implantable medical device 12 and external medical device 26 include circuitry for recording into a short-term, volatile memory telemetered signals stored for later retrieval, which become part of a set of device and derived measures, such as described below, by way of example, with reference to FIG. 2. Exemplary implantable medical devices suitable for use in the present invention include the Discovery line of pacemakers, manufactured by Guidant Corporation, Indianapolis, Ind., and the Gem line of ICDs, manufactured by Medtronic Corporation, Minneapolis, Minn.

The telemetered signals stored in the implantable medical device 12 are preferably retrieved upon the completion of an initial observation period and subsequently thereafter on a continuous, periodic (daily) basis, such as described in the related, commonly assigned U.S. Pat. No. 6,221,011, issued Apr. 24, 2001, the disclosure of which is incorporated herein by reference. A programmer 14, personal computer 18, or similar device for communicating with an implantable medical device 12 can be used to retrieve the telemetered signals. A magnetized reed switch (not shown) within the implantable medical device 12 closes in response to the placement of a wand 13 over the site of the implantable medical device 12. The programmer 14 sends programming or interrogating instructions to and retrieves stored telemetered signals from the implantable medical device 12 via RF signals exchanged through the wand 13. Similar communication means are used for accessing the external medical device 26. Once downloaded, the telemetered signals are sent via an internetwork 15, such as the Internet, to a server system 16 which periodically receives and stores the telemetered signals as device measures in patient care records 23 in a database 17, as further described below, by way of example, with reference to FIGS. 2 and 3. An exemplary programmer 14 suitable for use in the present invention is the Model 2901 Programmer Recorder Monitor, manufactured by Guidant Corporation, Indianapolis, Ind.

The patient 11 is remotely monitored by the server system 16 via the internetwork 15 through the periodic receipt of the retrieved device measures from the implantable medical device 12 or external medical device 26. The patient care records 23 in the database 17 are organized into two identified sets of device measures: an optional reference baseline 26 recorded during an initial observation period and monitoring sets 27 recorded subsequently thereafter. The device measures sets are periodically analyzed and compared by the server system 16 to indicator thresholds corresponding to quantifiable physiological measures of a pathophysiology indicative of respiratory insufficiency, as further described below with reference to FIG. 5. As necessary, feedback is provided to the patient 11. By way of example, the feedback includes an electronic mail message automatically sent by the server system 16 over the internetwork 15 to a personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. Moreover, simultaneous notifications can also be delivered to the patient's physician, hospital, or emergency medical services provider 29 using similar feedback means to deliver the information.

The server system 10 can consist of either a single computer system or a cooperatively networked or clustered set of computer systems. Each computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage, as is known in the art.

The database 17 stores patient care records 23 for each individual patient to whom remote patient care is being provided. Each patient care record 23 contains normal patient identification and treatment profile information, as well as medical history, medications taken, height and weight, and other pertinent data (not shown). The patient care records 23 consist primarily of two sets of data: device and derived measures (D&DM) sets 24a, 24b and quality of life (QOL) sets 25a, 25b, the organization of which are further described below with respect to FIGS. 2 and 3, respectively. The device and derived measures sets 24a, 24b and quality of life and symptom measures sets 25a, 25b can be further logically categorized into two potentially overlapping sets. The reference baseline 26 is a special set of device and derived reference measures sets 24a and quality of life and symptom measures sets 25a recorded and determined during an initial observation period. Monitoring sets 27 are device and derived measures sets 24b and quality of life and symptom measures sets 25b recorded and determined thereafter on a regular, continuous basis. Other forms of database organization are feasible.

Figure 2:
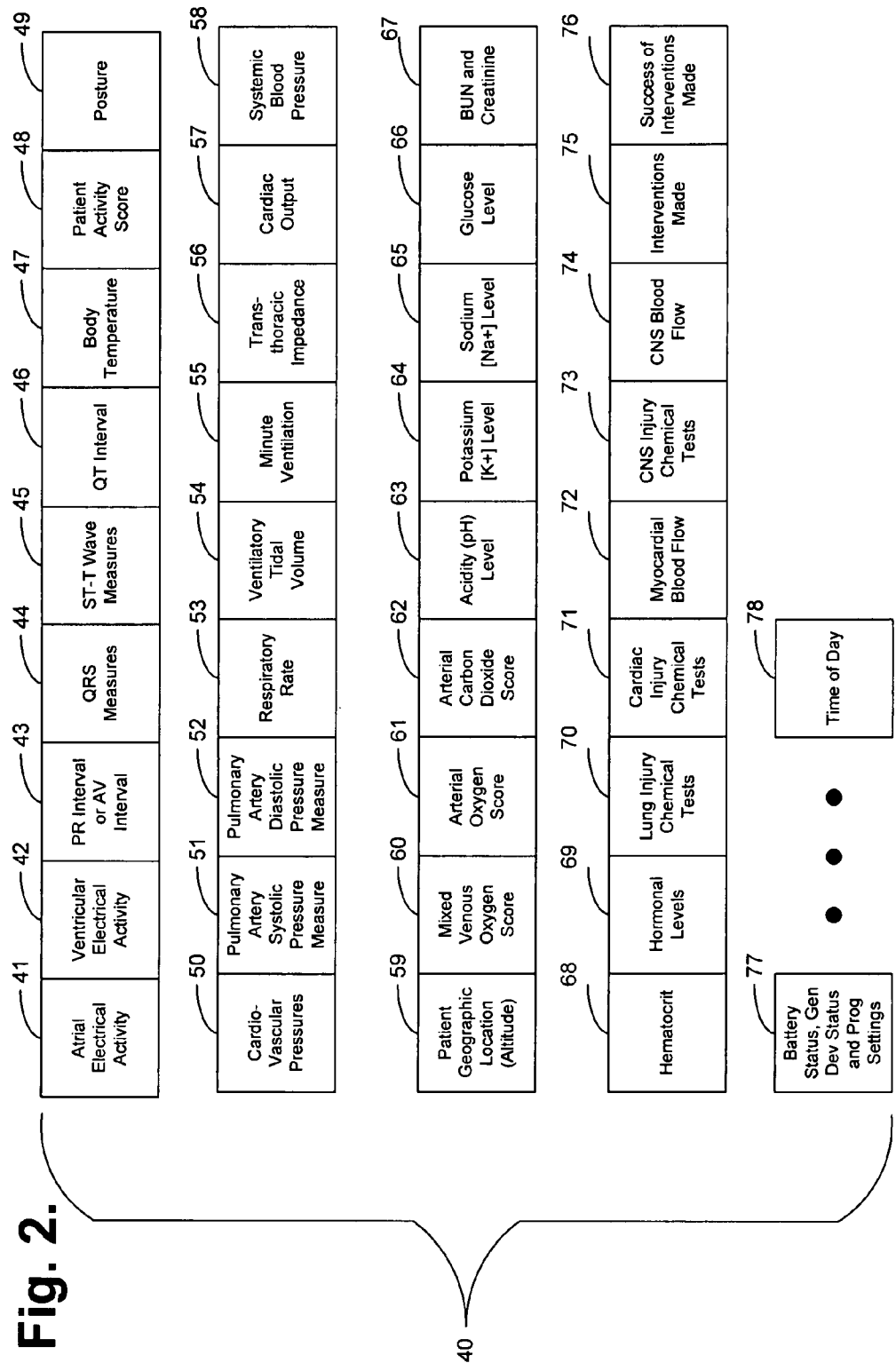
FIG. 2 is a database schema showing, by way of example, the organization of a device and derived measures set record for care of patients with respiratory insufficiency stored as part of a patient care record in the database of the system of FIG. 1.

The implantable medical device 12 and, in a more limited fashion, the external medical device 26, record patient information for care of patients with respiratory insufficiency on a regular basis. The recorded patient information is downloaded and stored in the database 17 as part of a patient care record 23. Further patient information can be derived from recorded data, as is known in the art. FIG. 2 is a database schema showing, by way of example, the organization of a device and derived measures set record 40 for patient care stored as part of a patient care record in the database 17 of the system of FIG. 1. Each record 40 stores patient information which includes a snapshot of telemetered signals data which were recorded by the implantable medical device 12 or the external medical device 26, for instance, on per heartbeat, binned average or derived bases; measures derived from the recorded device measures; and manually collected information, such as obtained through a patient medical history interview or questionnaire. The following non-exclusive information can be recorded for a patient: atrial electrical activity 41, ventricular electrical activity 42, PR interval or AV interval 43, QRS measures 44, ST-T wave measures 45, QT interval 46, body temperature 47, patient activity score 48, posture 49, cardiovascular pressures 50, pulmonary artery systolic pressure measure 51, pulmonary artery diastolic pressure measure 52, respiratory rate 53, ventilatory tidal volume 54, minute ventilation 55, transthoracic impedance 56, cardiac output 57, systemic blood pressure 58, patient geographic location (altitude) 59, mixed venous oxygen score 60, arterial oxygen score 61, arterial carbon dioxide score 62, acidity (pH) level 63, potassium [K+] level 64, sodium [Na+] level 65, glucose level 66, blood urea nitrogen (BUN) and creatinine 67, hematocrit 68, hormonal levels 69, lung injury chemical tests 70, cardiac injury chemical tests 71, myocardial blood flow 72, central nervous system (CNS) injury chemical tests 73, central nervous system blood flow 74, interventions made by the implantable medical device or external medical device 75, and the relative success of any interventions made 76. In addition, the implantable medical device or external medical device communicates device-specific information, including battery status, general device status and program settings 77 and the time of day 78 for the various recorded measures. Other types of collected, recorded, combined, or derived measures are possible, as is known in the art.

Figure 3:
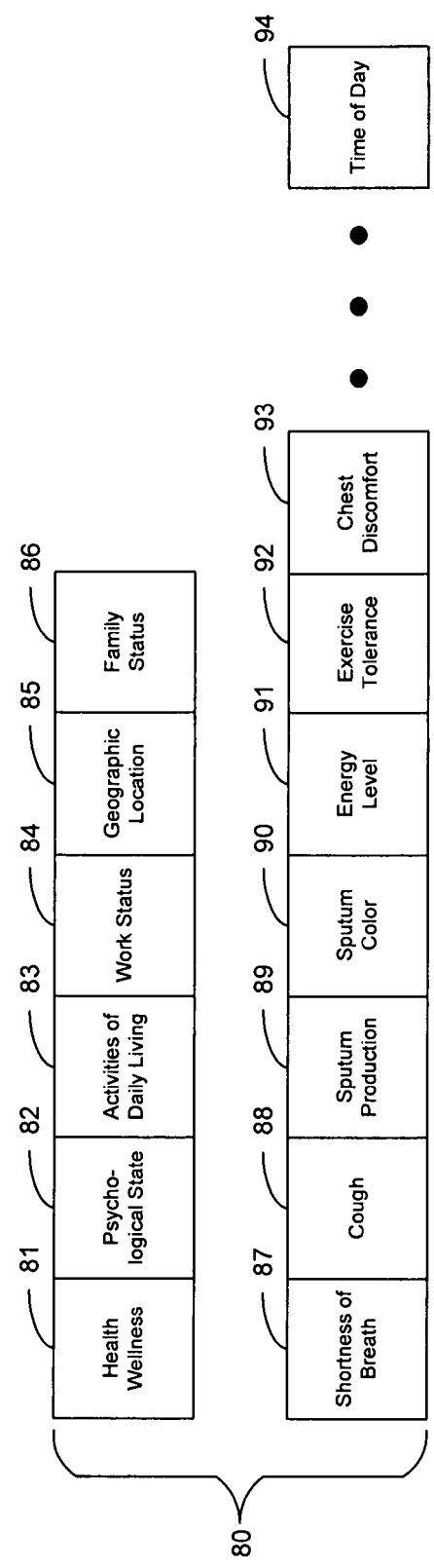
FIG. 3 is a database schema showing, by way of example, the organization of a quality of life and symptom measures set record for care of patients with respiratory insufficiency stored as part of a patient care record in the database of the system of FIG. 1.

The device and derived measures sets 24a, 24b (shown in FIG. 1), along with quality of life and symptom measures sets 25a, 25b, as further described below with reference to FIG. 3, are continuously and periodically received by the server system 16 as part of the on-going patient care monitoring and analysis function. These regularly collected data sets are collectively categorized as the monitoring sets 27 (shown in FIG. 1). In addition, select device and derived measures sets 24a and quality of life and symptom measures sets 25a can be designated as a reference baseline 26 at the outset of patient care to improve the accuracy and meaningfulness of the serial monitoring sets 27. Select patient information is collected, recorded, and derived during an initial period of observation or patient care, such as described in the related, commonly assigned U.S. Pat. No. 6,221,011, issued Apr. 24, 2001, the disclosure of which is incorporated herein by reference.

As an adjunct to remote patient care through the monitoring of measured physiological data via the implantable medical device 12 or external medical device 26, quality of life and symptom measures sets 25a can also be stored in the database 17 as part of the reference baseline 26, if used, and the monitoring sets 27. A quality of life measure is a semi-quantitative self-assessment of an individual patient's physical and emotional well being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16. FIG. 3 is a database schema showing, by way of example, the organization of a quality of life record 80 for use in the database 17. The following information is recorded for a patient: overall health wellness 81, psychological state 82, activities of daily living 83, work status 84, geographic location 85, family status 86, shortness of breath 87, cough 88, sputum production 89, sputum color 90, energy level 91, exercise tolerance 92, chest discomfort 93, and time of day 94, and other quality of life and symptom measures as would be known to one skilled in the art.

The patient may also add non-device quantitative measures, such as the six-minute walk distance, as complementary data to the device and derived measures sets 24a, 24b and the symptoms during the six-minute walk to quality of life and symptom measures sets 25a, 25b.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452-454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, adapted for use for lung disease rather than heart disease, also described in Ibid.

Figure 4:
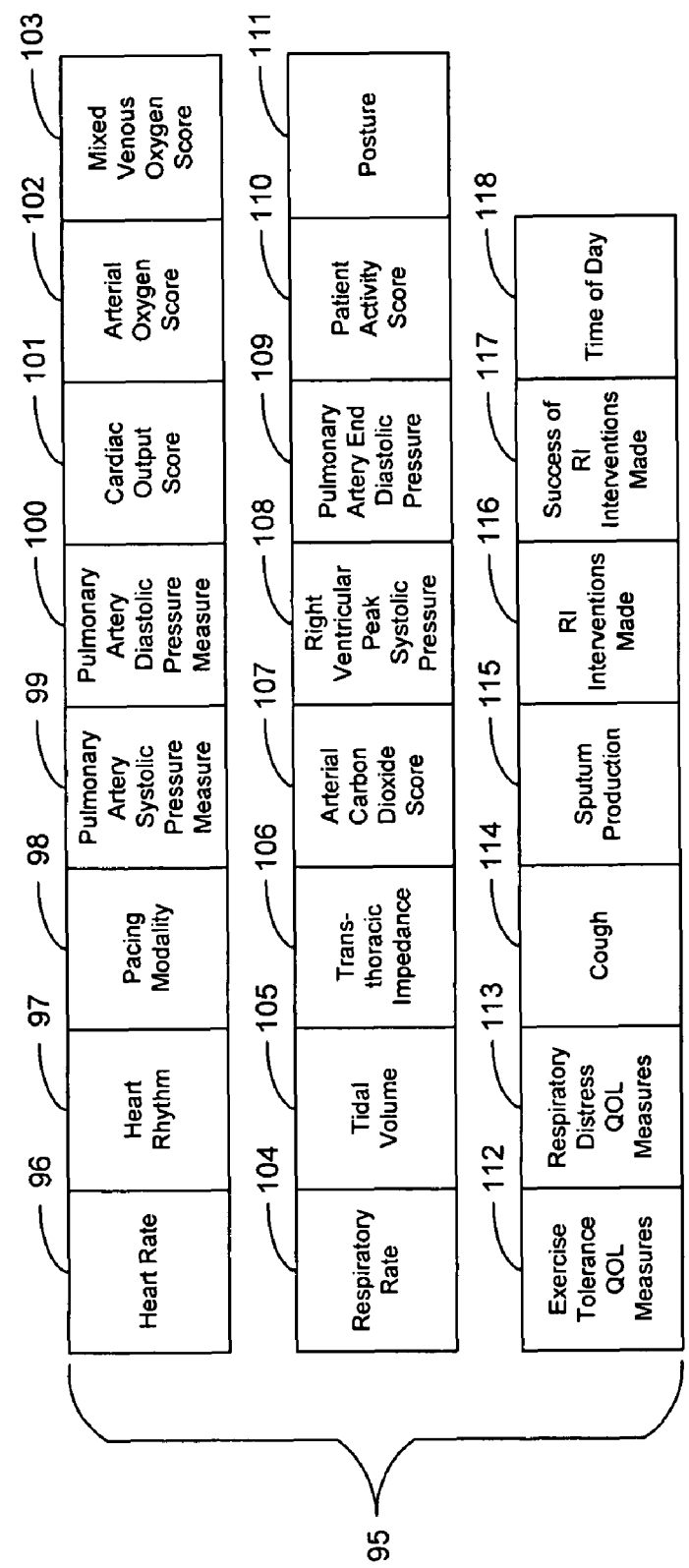
FIG. 4 is a database schema showing, by way of example, the organization of a combined measures set record for care of patients with respiratory insufficiency stored as part of a patient care record in the database of the system of FIG. 1.

On a periodic basis, the patient information stored in the database 17 is analyzed and compared to pre-determined cutoff levels, which, when exceeded, can provide etiological indications of respiratory insufficiency symptoms. FIG. 4 is a database schema showing, by way of example, the organization of a combined measures set record 95 for use in the database 17. Each record 95 stores patient information obtained or derived from the device and derived measures sets 24a, 24b and quality of life and symptom measures sets 25a, 25b as maintained in the reference baseline 26, if used, and the monitoring sets 27. The combined measures set 95 represents those measures most (but not exhaustively or exclusively) relevant to a pathophysiology indicative of respiratory insufficiency and are determined as further described below with reference to FIGS. 8A-8B. The following information is stored for a patient: heart rate 96, heart rhythm (e.g., normal sinus vs. atrial fibrillation) 97, pacing modality 98, pulmonary artery systolic pressure measure 99, pulmonary artery diastolic pressure measure 100, cardiac output score 101, arterial oxygen score 102, mixed venous oxygen score 103, respiratory rate 104, tidal volume 105, transthoracic impedance 106, arterial carbon dioxide score 107, right ventricular peak systolic pressure 108, pulmonary artery end diastolic pressure 109, patient activity score 110, posture 111, exercise tolerance quality of life and symptom measures 112, respiratory distress quality of life and symptom measures 113, cough 114, sputum production 115, any interventions made to treat respiratory insufficiency 116, including treatment by medical device, via drug infusion administered by the patient or by a medical device, surgery, and any other form of medical intervention as is known in the art, the relative success of any such interventions made 117, and time of day 118. Other types of comparison measures regarding respiratory insufficiency are possible as is known in the art. In the described embodiment, each combined measures set 95 is sequentially retrieved from the database 17 and processed. Alternatively, each combined measures set 95 could be stored within a dynamic data structure maintained transitorily in the random access memory of the server system 16 during the analysis and comparison operations.

Figure 5:
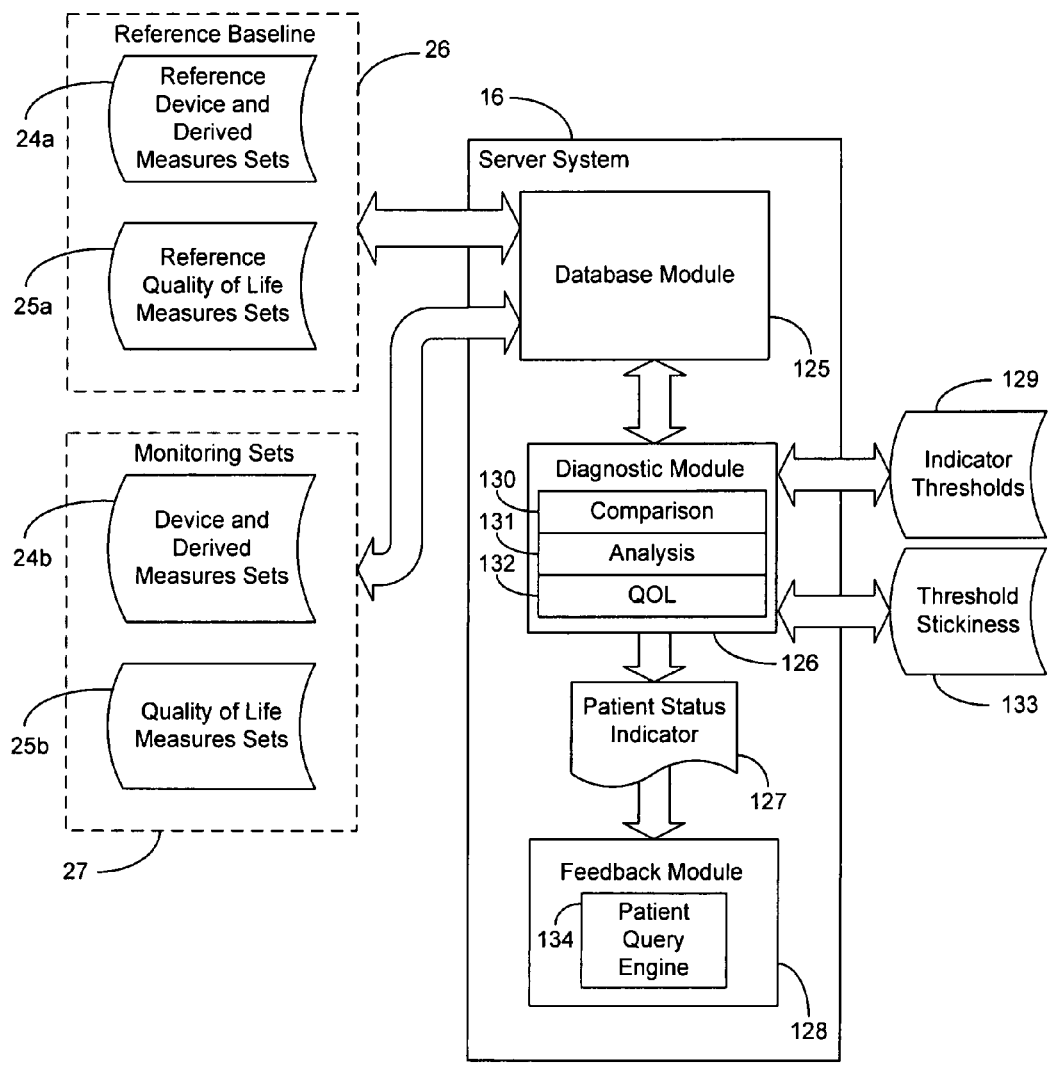
FIG. 5 is a block diagram showing the software modules of the server system of the system of FIG. 1.

FIG. 5 is a block diagram showing the software modules of the server system 16 of the system 10 of FIG. 1. Each module is a computer program written as source code in a conventional programming language, such as the C or Java programming languages, and is presented for execution by the CPU of the server system 16 as object or byte code, as is known in the art. The various implementations of the source code and object and byte codes can be held on a computer-readable storage medium or embodied on a transmission medium in a carrier wave. The server system 16 includes three primary software modules, database module 125, diagnostic module 126, and feedback module 128, which perform integrated functions as follows.

First, the database module 125 organizes the individual patient care records 23 stored in the database 17 (shown in FIG. 1) and efficiently stores and accesses the reference baseline 26, monitoring sets 27, and patient care data maintained in those records. Any type of database organization could be utilized, including a flat file system, hierarchical database, relational database, or distributed database, such as provided by database vendors, such as Oracle Corporation, Redwood Shores, Calif.

Next, the diagnostic module 126 makes findings of respiratory insufficiency based on the comparison and analysis of the data measures from the reference baseline 26 and monitoring sets 27. The diagnostic module includes three modules: comparison module 130, analysis module 131, and quality of life module 132. The comparison module 130 compares recorded and derived measures retrieved from the reference baseline 26, if used, and monitoring sets 27 to indicator thresholds 129. The database 17 stores individual patient care records 23 for patients suffering from various health disorders and diseases for which they are receiving remote patient care. For purposes of comparison and analysis by the comparison module 130, these records can be categorized into peer groups containing the records for those patients suffering from similar disorders, as well as being viewed in reference to the overall patient population. The definition of the peer group can be progressively refined as the overall patient population grows. To illustrate, FIG. 6 is a record view showing, by way of example, a set of partial patient care records for care of patients with respiratory insufficiency stored in the database 17 for three patients, Patient 1, Patient 2, and Patient 3. For each patient, three sets of peer measures, X, Y, and Z, are shown. Each of the measures, X, Y, and Z, could be either collected or derived measures from the reference baseline 26, if used, and monitoring sets 27.

The same measures are organized into time-based sets with Set 0 representing sibling measures made at a reference time $t=0$. Similarly, Set n−2, Set n−1 and Set n each represent sibling measures made at later reference times $t=n-2$, $t=n-1$ and $t=n$, respectively. Thus, for a given patient, such as Patient 1, serial peer measures, such as peer measure $X_0$ through $X_n$, represent the same type of patient information monitored over time. The combined peer measures for all patients can be categorized into a health disorder- or disease-matched peer group. The definition of disease-matched peer group is a progressive definition, refined over time as the number of monitored patients grows. Measures representing different types of patient information, such as measures $X_0$, $Y_0$, and $Z_0$, are sibling measures. These are measures which are also measured over time, but which might have medically significant meaning when compared to each other within a set for an individual patient.

The comparison module 130 performs two basic forms of comparisons. First, individual measures for a given patient can be compared to other individual measures for that same patient (self-referencing). These comparisons might be peer-to-peer measures, that is, measures relating to a one specific type of patient information, projected over time, for instance, $X_n, X_{n-1}, X_{n-2}, \ldots X_0$, or sibling-to-sibling measures, that is, measures relating to multiple types of patient information measured during the same time period, for a single snapshot, for instance, $X_n, Y_n,$ and $Z_n$, or projected over time, for instance, $X_n, Y_n, Z_n, X_{n-1}, Y_{n-1}, Z_{n-1}, X_{n-2}, Y_{n-2}, Z_{n-2}, \ldots X_0, Y_0, Z_0$. Second, individual measures for a given patient can be compared to other individual measures for a group of other patients sharing the same disorder- or disease-specific characteristics (peer group referencing) or to the patient population in general (population referencing). Again, these comparisons might be peer-to-peer measures projected over time, for instance, $X_n, X_{n'}, X_{n''}, X_{n-1}, X_{n-1'}, X_{n-1''}, X_{n-2}, X_{n-2'}, X_{n-2''}, \ldots X_0, X_{0'}, X_{0''}$, or comparing the individual patient's measures to an average from the group. Similarly, these comparisons might be sibling-to-sibling measures for single snapshots, for instance, $X_n, X_{n'}, X_{n''}, Y_n, Y_{n'}, Y_{n''},$ and $Z_n, Z_{n'}, Z_{n''}$, or projected over time, for instance, $X_n, X_{n'}, X_{n''}, Y_n, Y_{n'}, Y_{n''}, Z_n, Z_{n'}, Z_{n''}, X_{n-1}, X_{n-1'}, X_{n-1''}, Y_{n-1}, Y_{n-1'}, Y_{n-1''}, Z_{n-1}, Z_{n-1'}, Z_{n-1''}, X_{n-2}, X_{n-2'}, X_{n-2''}, Y_{n-2}, Y_{n-2'}, Y_{n-2''}, Z_{n-2}, Z_{n-2'}, Z_{n-2''} \ldots X_0, X_{0'}, X_{0''}, Y_0, Y_{0'}, Y_{0''},$ and $Z_0, Z_{0'}, Z_{0''}$. Other forms of comparisons are feasible, including multiple disease diagnoses for diseases exhibiting similar abnormalities in physiological measures that result from a second disease but manifest in different combinations or onset in different temporal sequences.

Figure 7:
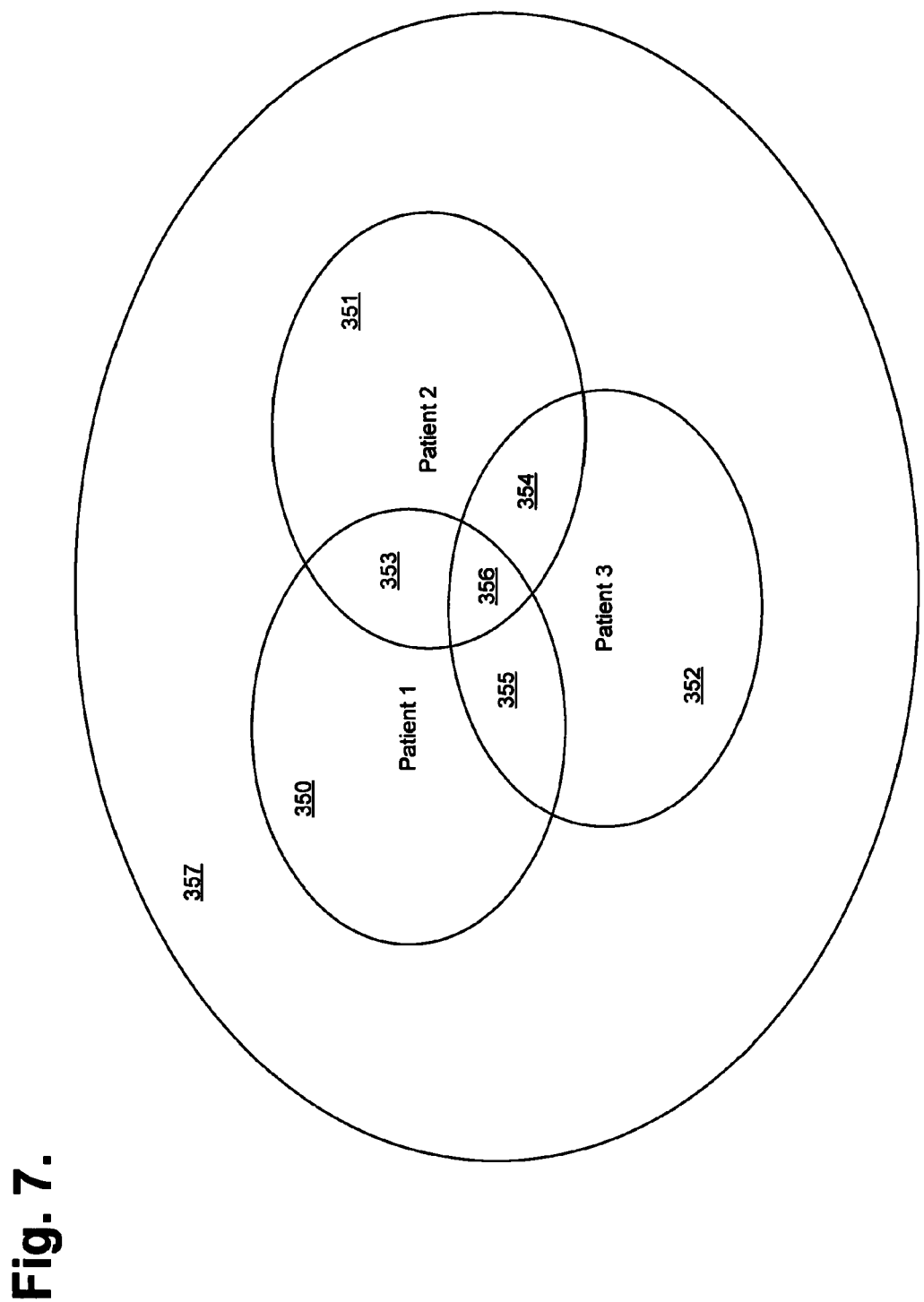
FIG. 7 is a Venn diagram showing, by way of example, peer group overlap between the partial patient care records of FIG. 6.

FIG. 7 is a Venn diagram showing, by way of example, peer group overlap between the partial patient care records 23 of FIG. 1. Each patient care record 23 includes characteristics data 350, 351, 352, including personal traits, demographics, medical history, and related personal data, for patients 1, 2 and 3, respectively. For example, the characteristics data 350 for patient 1 might include personal traits which include gender and age, such as male and an age between 40-45; a demographic of resident of New York City; and a medical history consisting of chronic bronchitis, recurrent pneumonia, a history of an inferior myocardial infarction and diabetes. Similarly, the characteristics data 351 for patient 2 might include identical personal traits, thereby resulting in partial overlap 353 of characteristics data 350 and 351. Similar characteristics overlap 354, 355, 356 can exist between each respective patient. The overall patient population 357 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 356 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

Referring back to FIG. 5, the analysis module 131 analyzes the results from the comparison module 130, which are stored as a combined measures set 95 (not shown), to a set of indicator thresholds 129, as further described below with reference to FIGS. 8A-8B. Similarly, the quality of life module 132 compares quality of life and symptom measures 25a, 25b from the reference baseline 26 and monitoring sets 27, the results of which are incorporated into the comparisons performed by the analysis module 131, in part, to either refute or support the findings based on physiological "hard" data. Finally, the feedback module 128 provides automated feedback to the individual patient based, in part, on the patient status indicator 127 generated by the diagnostic module 126. As described above, the feedback could be by electronic mail or by automated voice mail or facsimile. The feedback can also include normalized voice feedback, such as described in the related, commonly assigned U.S. Pat. No. 6,203,495, issued Mar. 20, 2001, the disclosure of which is incorporated herein by reference. In addition, the feedback module 128 determines whether any changes to interventive measures are appropriate based on threshold stickiness ("hysteresis") 133, as further described below with reference to FIG. 16. The threshold stickiness 133 can prevent fickleness in the diagnostic routines resulting from transient, non-trending and non-significant fluctuations in the various collected and derived measures in favor of more certainty in diagnosis. However, in the case of some of the parameters being followed, such as activity and pulmonary artery systolic and diastolic pressures, abrupt spikes in these measures can be indicative of coughing and therefore helpful in indicating the onset of pulmonary insufficiency. In a further embodiment of the present invention, the feedback module 128 includes a patient query engine 134 that enables the individual patient 11 to interactively query the server system 16 regarding the diagnosis, therapeutic maneuvers, and treatment regimen. Conversely, the patient query engines 134, found in interactive expert systems for diagnosing medical conditions, can interactively query the patient. Using the personal computer 18 (shown in FIG. 1), the patient can have an interactive dialogue with the automated server system 16, as well as human experts as necessary, to self assess his or her medical condition. Such expert systems are well known in the art, an example of which is the MYCIN expert system developed at Stanford University and described in Buchanan, B. & Shortlife, E., "RULE-BASED EXPERT SYSTEMS. The MYCIN Experiments of the Stanford Heuristic Programming Project," Addison-Wesley (1984). The various forms of feedback described above help to increase the accuracy and specificity of the reporting of the quality of life and symptomatic measures.

Figure 8A:
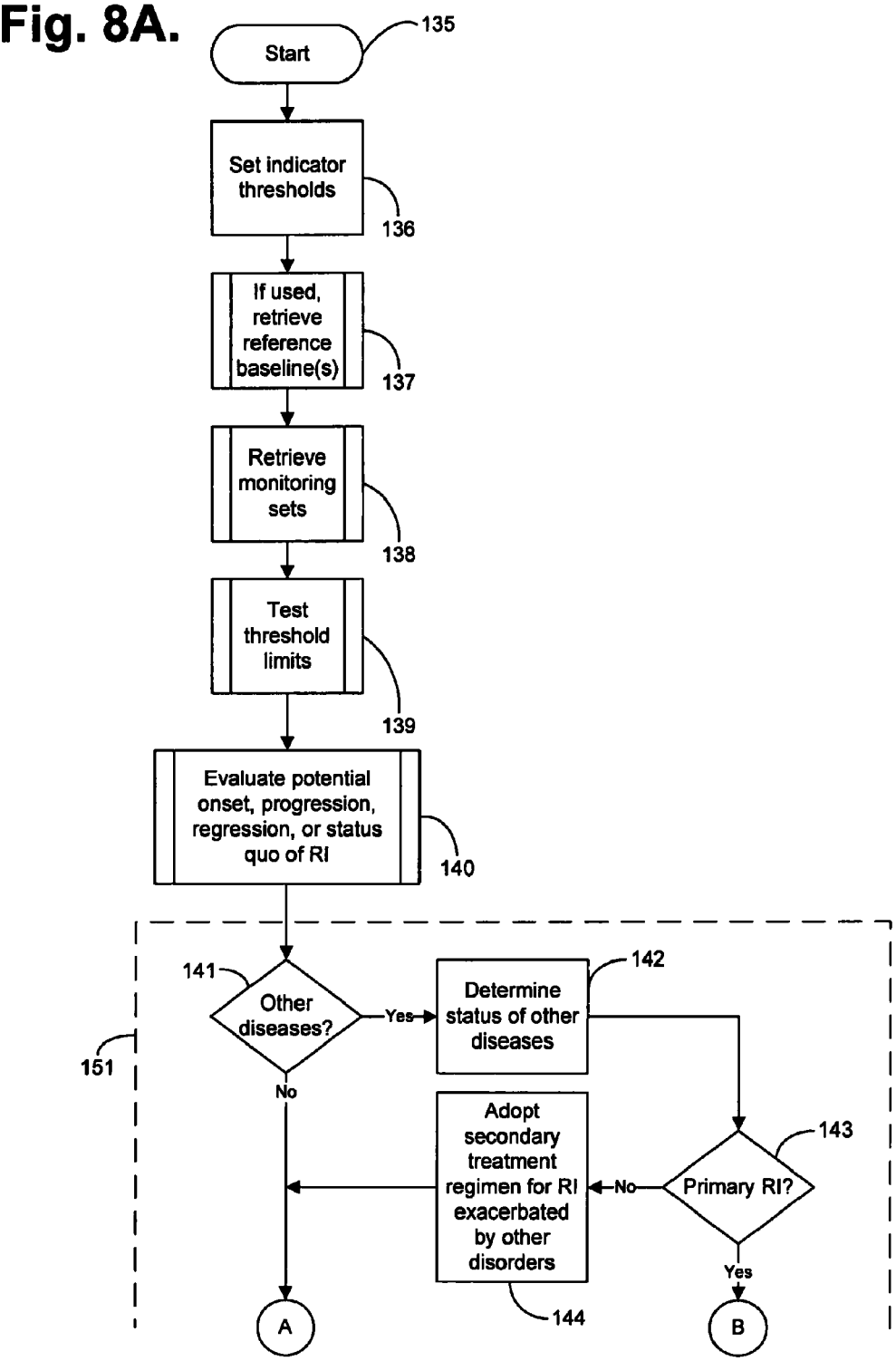
FIGS. 8A-8B are flow diagrams showing a method for diagnosing and monitoring respiratory insufficiency using an automated patient care system in accordance with the present invention.
Figure 8B:
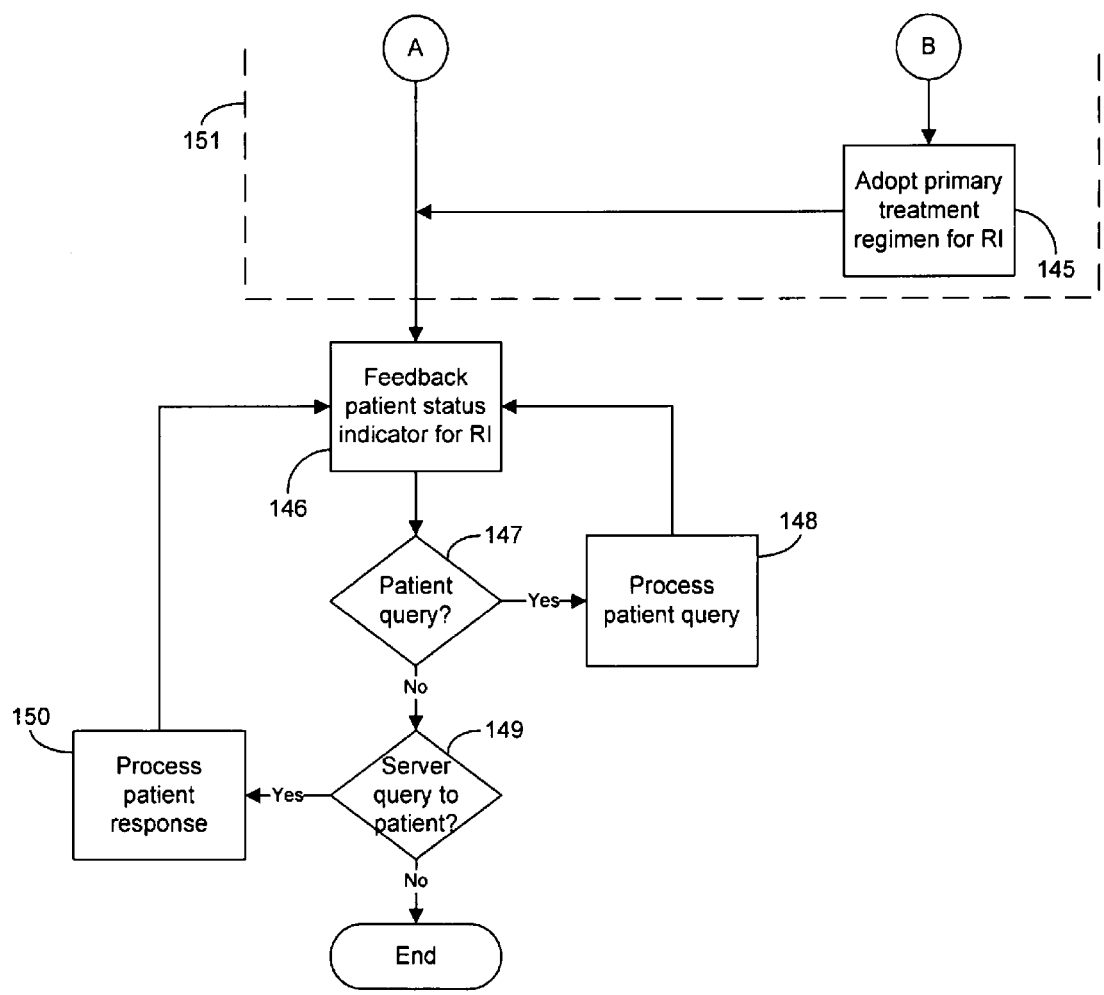

FIGS. 8A-8B are flow diagrams showing a method for diagnosing and monitoring respiratory insufficiency and outcomes thereof 135 using an automated collection and analysis patient care system 10 in accordance with the present invention. First, the indicator thresholds 129 (shown in FIG. 5) are set (block 136) by defining a quantifiable physiological measure of a pathophysiology indicative of respiratory insufficiency and relating to the each type of patient information in the combined device and derived measures set 95 (shown in FIG. 4). The actual values of each indicator threshold can be finite cutoff values, weighted values, or statistical ranges, as discussed below with reference to FIGS. 11A-11F. Next, the reference baseline 26 (block 137) and monitoring sets 27 (block 138) are retrieved from the database 17, as further described below with reference to FIGS. 9 and 10, respectively. Each measure in the combined device and derived measures set 95 is tested against the threshold limits defined for each indicator threshold 129 (block 139), as further described below with reference to FIGS. 11A-11F. The potential onset, progression, regression, or status quo of respiratory insufficiency is then evaluated (block 140) based upon the findings of the threshold limits tests (block 139), as further described below with reference to FIGS. 13A-13C, 14A-14C, 15A-15C.

In a further embodiment, multiple near-simultaneous disorders are considered in addition to primary respiratory insufficiency. Primary respiratory insufficiency is defined as the onset or progression of respiratory insufficiency without obvious inciting cause. Secondary respiratory insufficiency is defined as the onset or progression of respiratory insufficiency (in a patient with or without pre-existing respiratory insufficiency) from another disease process, such as congestive heart failure, coronary insufficiency, atrial fibrillation, and so forth. Other health disorders and diseases can potentially share the same forms of symptomatology as respiratory insufficiency, such as congestive heart failure, myocardial ischemia, pneumonia, exacerbation of chronic bronchitis, renal failure, sleep-apnea, stroke, anemia, atrial fibrillation, other cardiac arrhythmias, and so forth. If more than one abnormality is present, the relative sequence and magnitude of onset of abnormalities in the monitored measures becomes most important in sorting and prioritizing disease diagnosis and treatment.

Thus, if other disorders or diseases are being cross-referenced and diagnosed (block 141), their status is determined (block 142). In the described embodiment, the operations of ordering and prioritizing multiple near-simultaneous disorders (box 151) by the testing of threshold limits and analysis in a manner similar to congestive heart failure as described above, preferably in parallel to the present determination, is described in the related, commonly assigned U.S. Pat. No. 6,440,066, entitled "Automated Collection And Analysis Patient Care System And Method For Ordering And Prioritizing Multiple Health Disorders To Identify An Index Disorder," issued Aug. 27, 2002, the disclosure of which is incorporated herein by reference. If respiratory insufficiency is due to an obvious inciting cause, i.e., secondary respiratory insufficiency, (block 143), an appropriate treatment regimen for respiratory insufficiency as exacerbated by other disorders is adopted that includes treatment of secondary disorders, e.g., congestive heart failure, myocardial ischemia, atrial fibrillation, and so forth (block 144) and a suitable patient status indicator 127 for respiratory insufficiency is provided (block 146) to the patient. Suitable devices and approaches to diagnosing and treating congestive heart failure, myocardial infarction, and atrial fibrillation are described in related, commonly assigned U.S. Pat. No. 6,336,903, entitled "Automated Collection And Analysis Patient Care System And Method For Diagnosing And Monitoring Congestive Heart Failure And Outcomes Thereof," issued Jan. 8, 2002; U.S. Pat. No. 6,368,284, entitled "Automated Collection And Analysis Patient Care System And Method For Diagnosing And Monitoring Myocardial Ischemia And Outcomes Thereof," issued Apr. 9, 2002; and U.S. Pat. No. 6,411,840, entitled "Automated Collection And Analysis Patient Care System And Method For Diagnosing And Monitoring The Outcomes Of Atrial Fibrillation," Jun. 15, 2002, the disclosures of which are incorporated herein by reference.

Otherwise, if primary respiratory insufficiency is indicated (block 143), a primary treatment regimen is followed (block 145). A patient status indicator 127 for respiratory insufficiency is provided (block 146) to the patient regarding physical well-being, disease prognosis, including any determinations of disease onset, progression, regression, or status quo, and other pertinent medical and general information of potential interest to the patient.

Finally, in a further embodiment, if the patient submits a query to the server system 16 (block 147), the patient query is interactively processed by the patient query engine (block 148). Similarly, if the server elects to query the patient (block 149), the server query is interactively processed by the server query engine (block 150). The method then terminates if no further patient or server queries are submitted.

Figure 9:
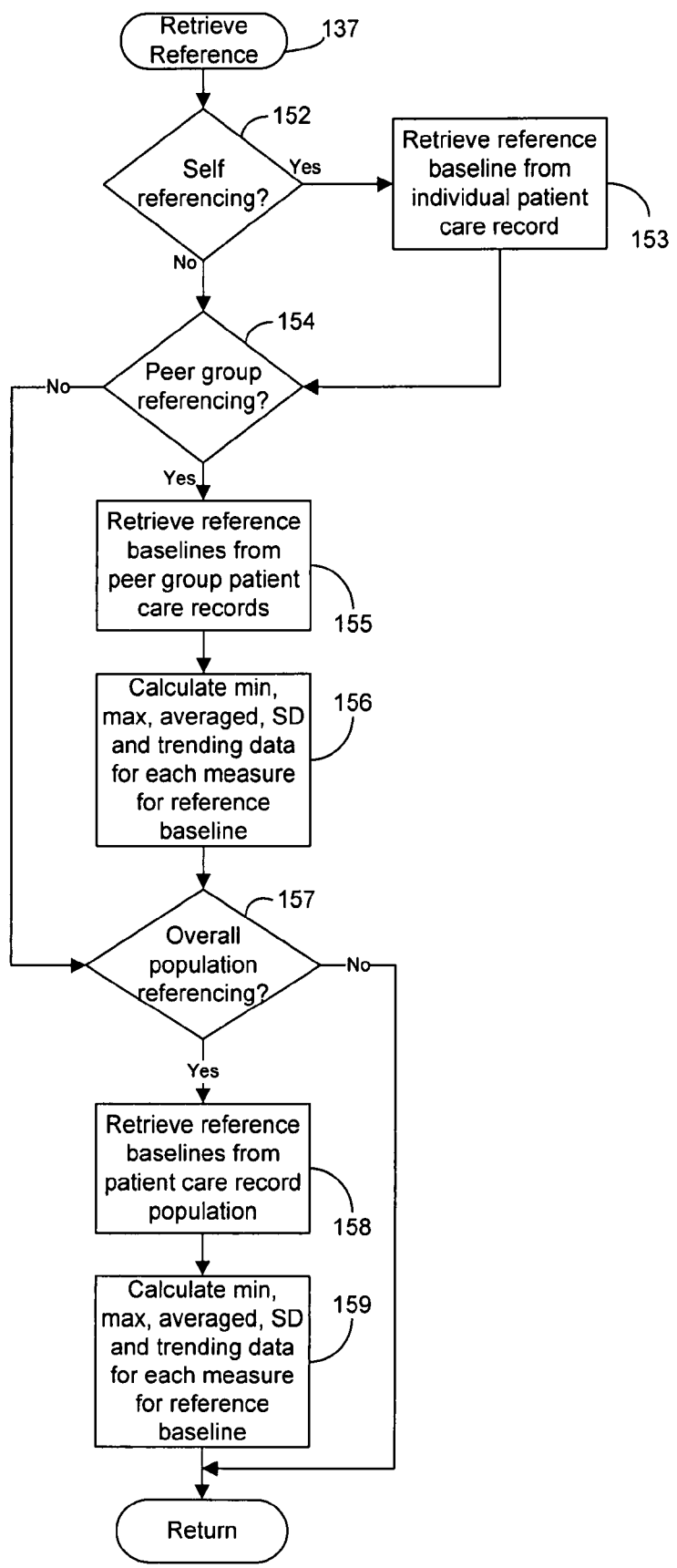
FIG. 9 is a flow diagram showing the routine for retrieving reference baseline sets for use in the method of FIGS. 8A-8B.

FIG. 9 is a flow diagram showing the routine for retrieving reference baseline sets 137 for use in the method of FIGS. 8A-8B. The purpose of this routine is to retrieve the appropriate reference baseline sets 26, if used, from the database 17 based on the types of comparisons being performed. First, if the comparisons are self referencing with respect to the measures stored in the individual patient care record 23 (block 152), the reference device and derived measures set 24a and reference quality of life and symptom measures set 25a, if used, are retrieved for the individual patient from the database 17 (block 153). Next, if the comparisons are peer group referencing with respect to measures stored in the patient care records 23 for a health disorder- or disease-specific peer group (block 154), the reference device and derived measures set 24a and reference quality of life and symptom measures set 25a, if used, are retrieved from each patient care record 23 for the peer group from the database 17 (block 155). Data for each measure (e.g., minimum, maximum, averaged, standard deviation (SD), and trending data) from the reference baseline 26 for the peer group is then calculated (block 156). Finally, if the comparisons are population referencing with respect to measures stored in the patient care records 23 for the overall patient population (block 157), the reference device and derived measures set 24a and reference quality of life and symptom measures set 25a, if used, are retrieved from each patient care record 23 from the database 17 (block 158). Minimum, maximum, averaged, standard deviation, and trending data and other numerical processes using the data, as is known in the art, for each measure from the reference baseline 26 for the peer group is then calculated (block 159). The routine then returns.

Figure 10:
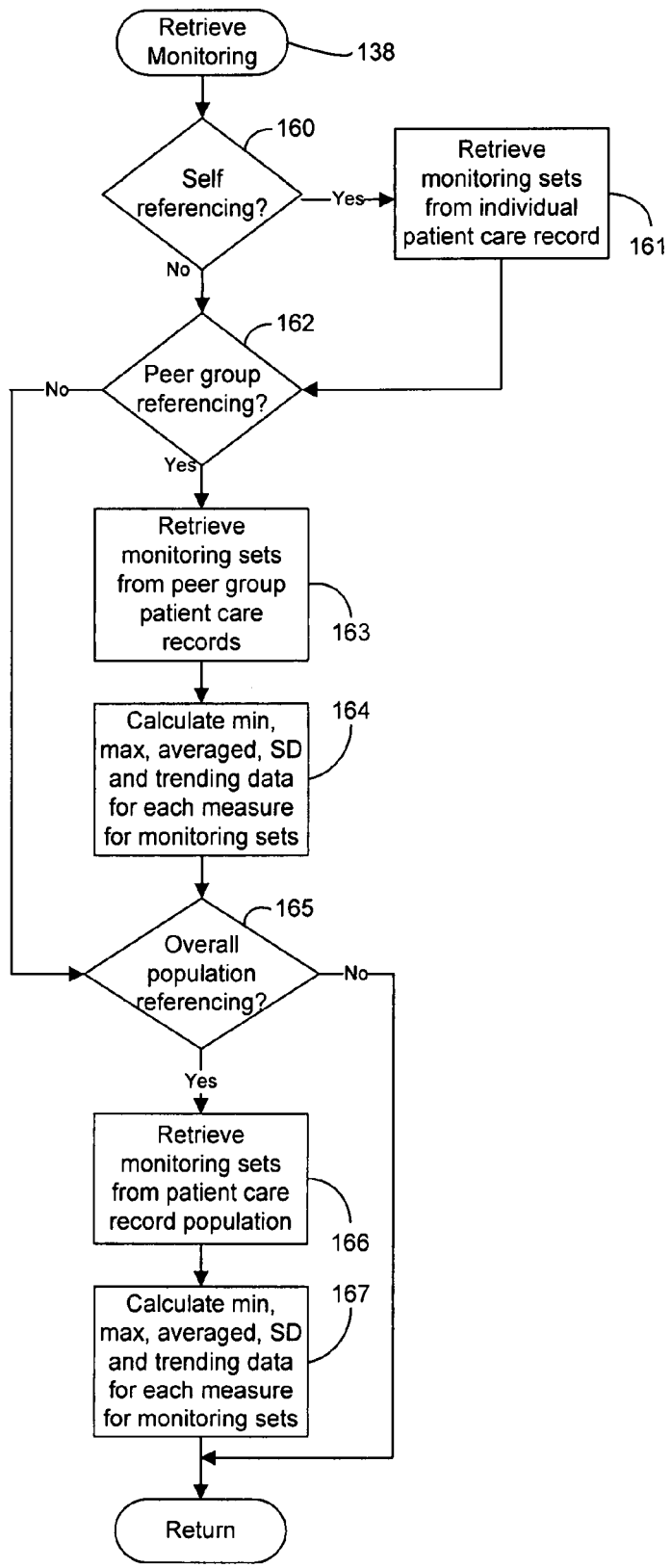
FIG. 10 is a flow diagram showing the routine for retrieving monitoring sets for use in the method of FIGS. 8A-8B.
Figure 11A:
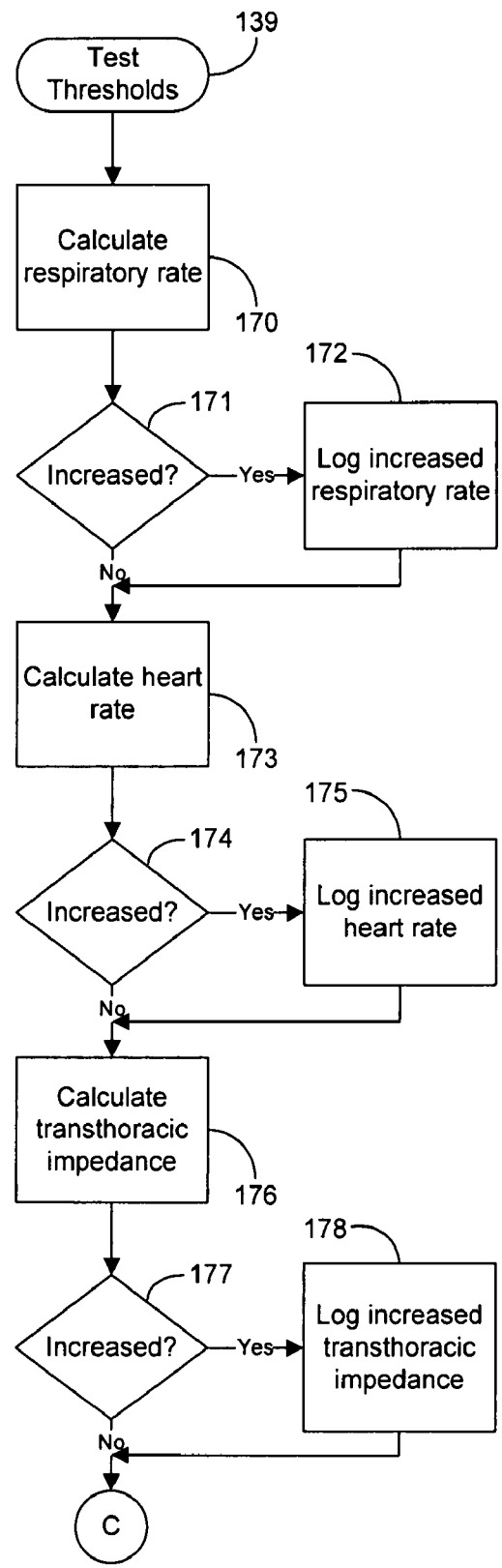
FIGS. 11A-11F are flow diagrams showing the routine for testing threshold limits for use in the method of FIGS. 8A-8B.
Figure 11B:
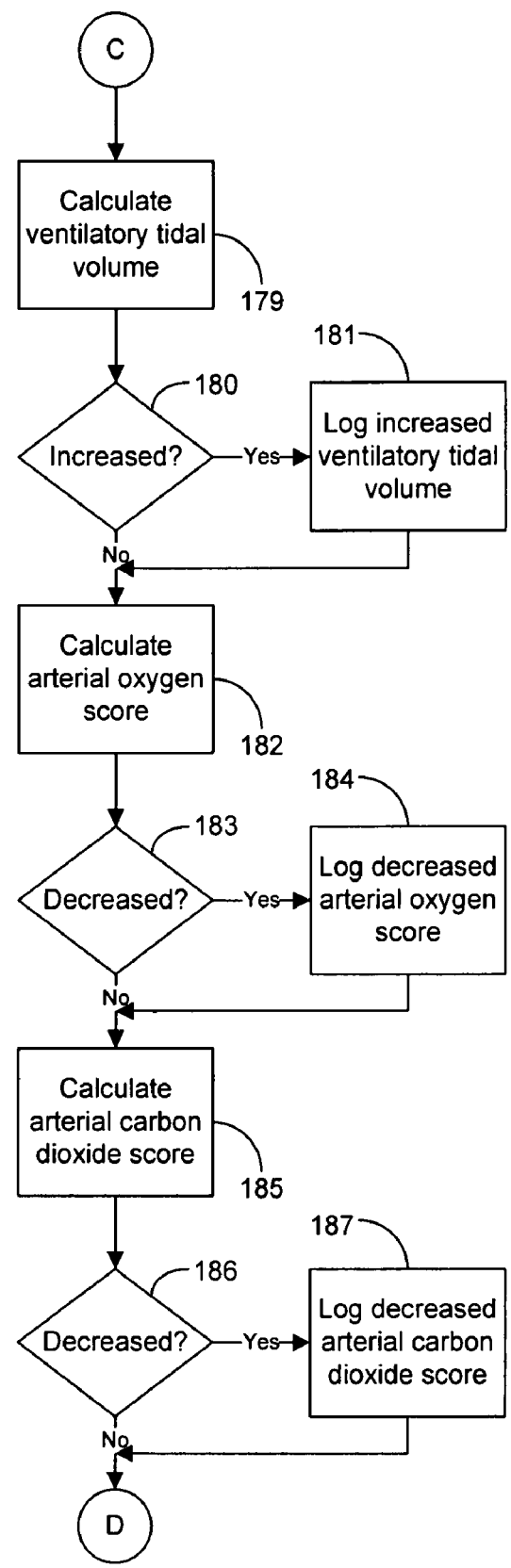
Figure 11C:
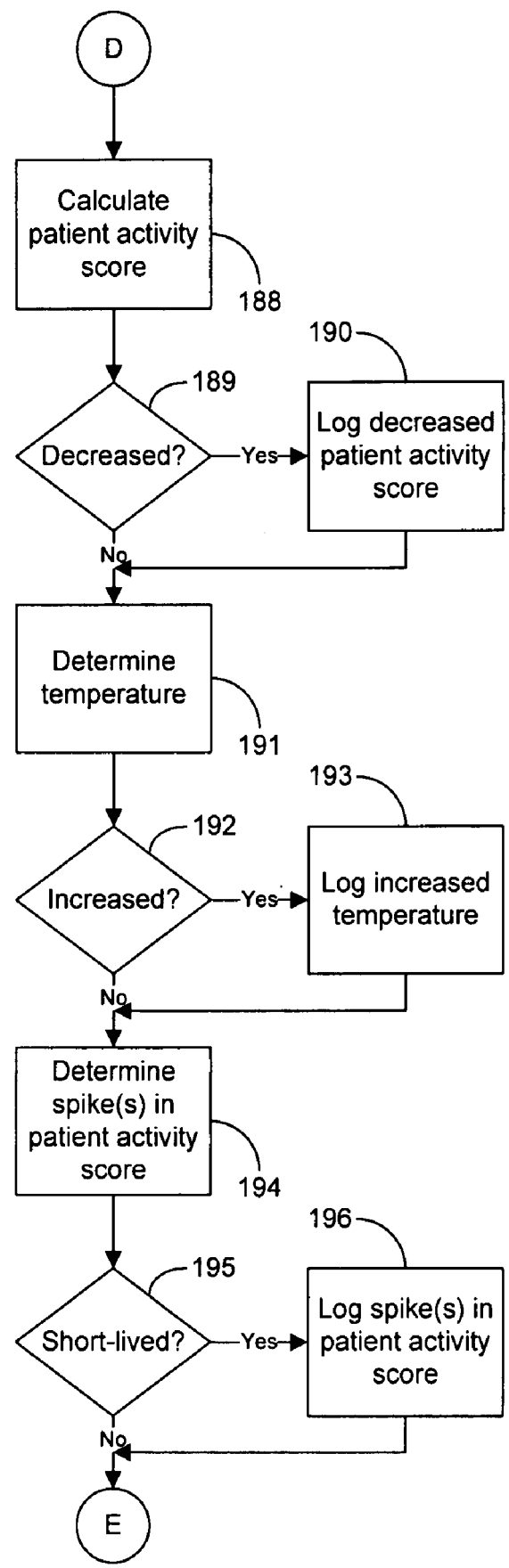
Figure 11D:
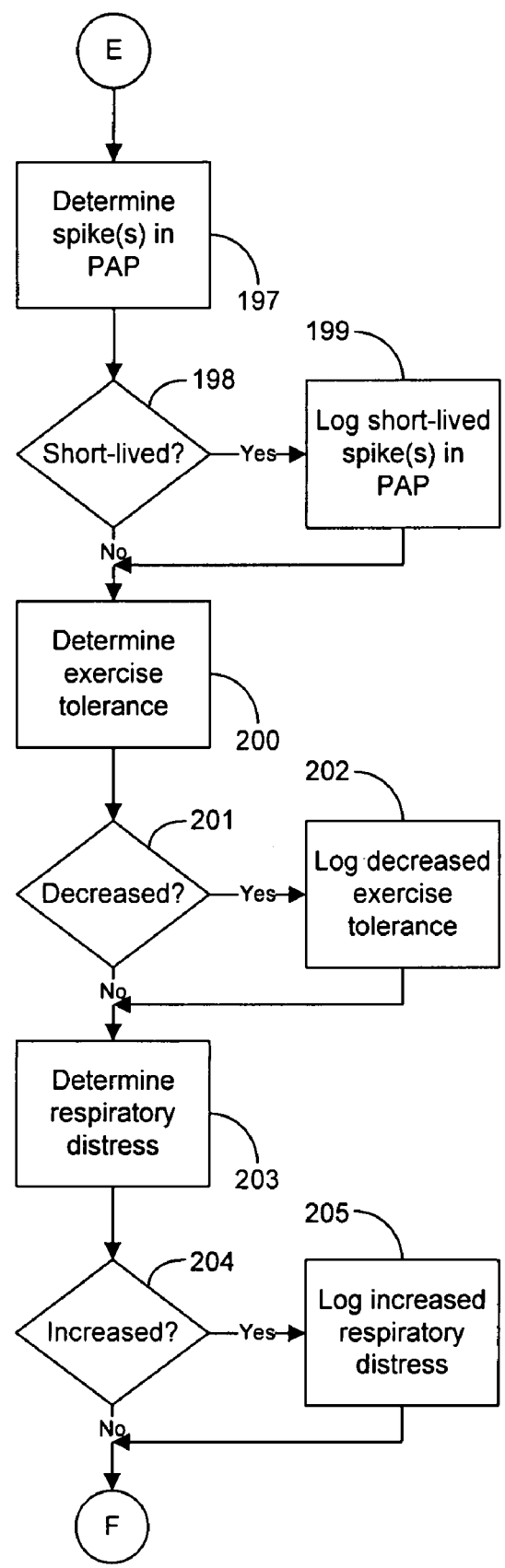
Figure 11E:
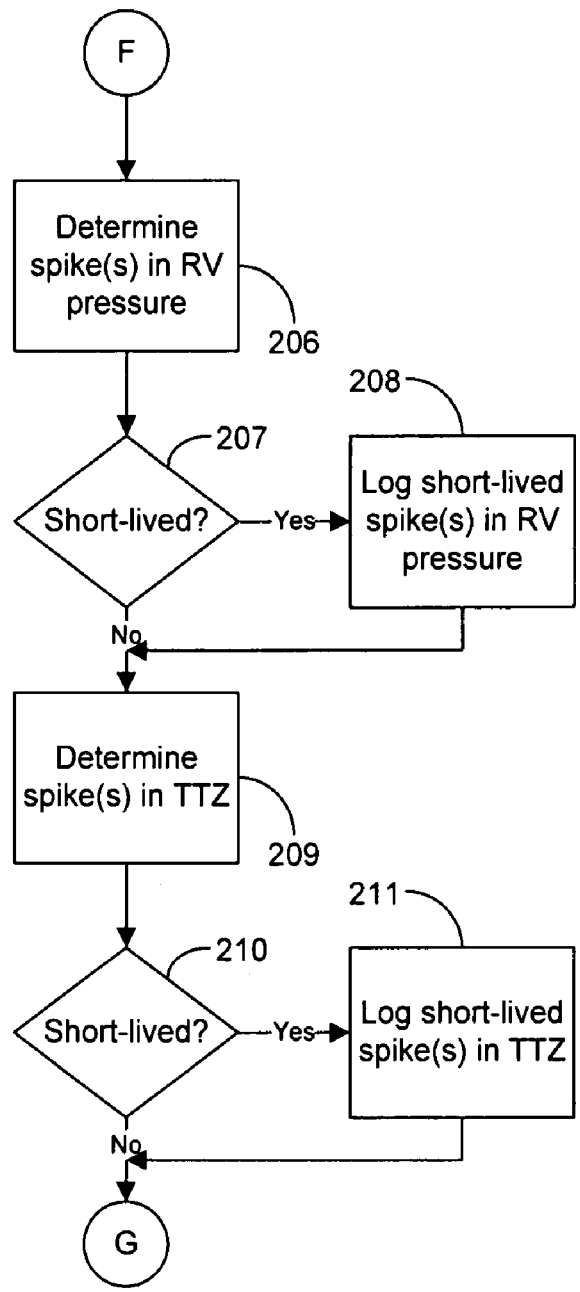
Figure 11F:
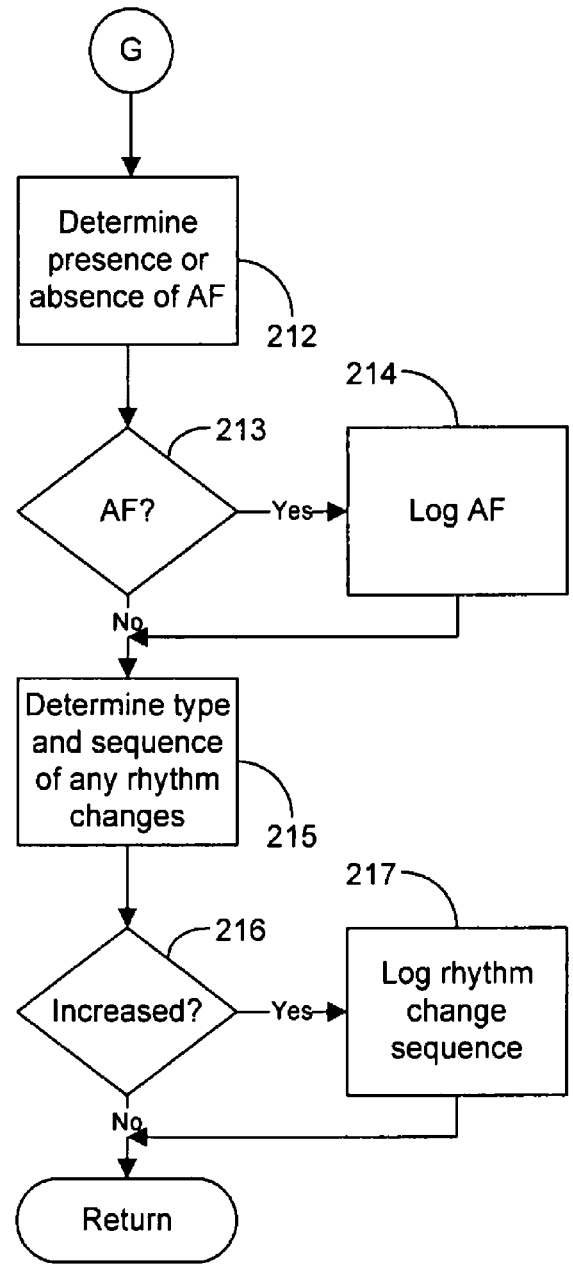

FIG. 10 is a flow diagram showing the routine for retrieving monitoring sets 138 for use in the method of FIGS. 8A-8B. The purpose of this routine is to retrieve the appropriate monitoring sets 27 from the database 17 based on the types of comparisons being performed. First, if the comparisons are self referencing with respect to the measures stored in the individual patient care record 23 (block 160), the device and derived measures set 24b and quality of life and symptom measures set 25b, if used, are retrieved for the individual patient from the database 17 (block 161). Next, if the comparisons are peer group referencing with respect to measures stored in the patient care records 23 for a health disorder- or disease-specific peer group (block 162), the device and derived measures set 24b and quality of life and symptom measures set 25b, if used, are retrieved from each patient care record 23 for the peer group from the database 17 (block 163). Data for each measure (e.g., minimum, maximum, averaged, standard deviation, and trending data) from the monitoring sets 27 for the peer group is then calculated (block 164). Finally, if the comparisons are population referencing with respect to measures stored in the patient care records 23 for the overall patient population (block 165), the device and derived measures set 24b and quality of life and symptom measures set 25b, if used, are retrieved from each patient care record 23 from the database 17 (block 166). Minimum, maximum, averaged, standard deviation, and trending data and other numerical processes using the data, as is known in the art, for each measure from the monitoring sets 27 for the peer group is then calculated (block 167). The routine then returns.

FIGS. 11A-11F are flow diagrams showing the routine for testing threshold limits 139 for use in the method of FIGS. 8A and 8B. The purpose of this routine is to analyze, compare, and 10 g any differences between the observed, objective measures stored in the reference baseline 26, if used, and the monitoring sets 27 to the indicator thresholds 129. Briefly, the routine consists of tests pertaining to each of the indicators relevant to diagnosing and monitoring respiratory insufficiency. The threshold tests focus primarily on: (1) changes to and rates of change for the indicators themselves, as stored in the combined device and derived measures set 95 (shown in FIG. 4) or similar data structure; and (2) violations of absolute threshold limits which trigger an alert. The timing and degree of change may vary with each measure and with the natural fluctuations noted in that measure during the reference baseline period. In addition, the timing and degree of change might also vary with the individual and the natural history of a measure for that patient.

One suitable approach to performing the threshold tests uses a standard statistical linear regression technique using a least squares error fit. The least squares error fit can be calculated as follows:

$$y = \beta_0 + \beta_1 x \quad (1)$$

$$\beta = \frac{SS_{xy}}{SS_{xx}} \quad (2)$$

$$SS_{xy} = \sum_{i=1}^{n} x_i y_i - \frac{\left(\sum_{i=1}^{n} x_i\right)\left(\sum_{i=1}^{n} y_i\right)}{n} \quad (3)$$

-continued $$SS_{xx} = \sum_{i=1}^{n} x_i^2 - \frac{\left(\sum_{i=1}^{n} x_i\right)^2}{n} \quad (4)$$

where n is the total number of measures, $x_i$ is the time of day for measure i, and $y_i$ is the value of measure i, $\beta_1$ is the slope, and $\beta_0$ is the y-intercept of the least squares error line. A positive slope $\beta_1$ indicates an increasing trend, a negative slope $\beta_1$ indicates a decreasing trend, and no slope indicates no change in patient condition for that particular measure. A predicted measure value can be calculated and compared to the appropriate indicator threshold 129 for determining whether the particular measure has either exceeded an acceptable threshold rate of change or the absolute threshold limit.

For any given patient, three basic types of comparisons between individual measures stored in the monitoring sets 27 are possible: self referencing, peer group, and general population, as explained above with reference to FIG. 6. In addition, each of these comparisons can include comparisons to individual measures stored in the pertinent reference baselines 24.

The indicator thresholds 129 for detecting a trend indicating progression into a state of respiratory insufficiency or a state of imminent or likely respiratory insufficiency, for example, over a one week time period, can be as follows:

(1) Respiratory rate (block 170): If the respiratory rate has increased over 1.0 SD from the mean respiratory rate in the reference baseline 26 (block 171), the increased respiratory rate and time span over which it occurs are logged in the combined measures set 95 (block 172).

(2) Heart rate (block 173): If the heart rate has increased over 1.0 SD from the mean heart rate in the reference baseline 26 (block 174), the increased heart rate and time span over which it occurs are logged in the combined measures set 95 (block 175).

(3) Transthoracic impedance (block 176): If the transthoracic impedance has increased over 1.0 SD from the mean transthoracic impedance in the reference baseline 26 (block 177), the increased transthoracic impedance and time span are logged in the combined measures set 95 (block 178).

(4) The ventilatory tidal volume (block 179): If the tidal volume has increased over 1.0 SD from the tidal volume score in the reference baseline 26 (block 180), the increased tidal volume score and time span are logged in the combined measures set 95 (block 181).

(5) Arterial oxygen score (block 182): If the arterial oxygen score has decreased over 1.0 SD from the arterial oxygen score in the reference baseline 26 (block 183), the decreased arterial oxygen score and time span are logged in the combined measures set 95 (block 184).

(6) Arterial carbon dioxide score (block 185): If the arterial carbon dioxide score has decreased over 1.0 SD from the arterial carbon dioxide score in the reference baseline 26 (block 186), the decreased arterial carbon dioxide score and time span are logged in the combined measures set 95 (block 187).

(7) Patient activity score (block 188): If the mean patient activity score has decreased over 1.0 SD from the mean patient activity score in the reference baseline 26 (block 189), the decreased patient activity score and time span are logged in the combined measures set 95 (block 190).

(8) Temperature (block 191): If the patient temperature score has increased over 1.0 SD from the mean patient temperature score in the reference baseline 26 (block 192), the increased patient temperature score and the time span are logged in the combined measures set 95 (block 193).

(9) Spikes in patient activity (block 194): If short-lived spikes in the patient activity score occur over time periods under 5 minutes compared to the reference baseline 26 (block 195), the spike in patient activity score and time span are logged in the combined measures set 95 (block 196).

(10) Spikes in pulmonary arterial pressure (PAP) (block 197): If short-lived spikes in the pulmonary arterial pressure score occur over time periods under 5 minutes compared to the reference baseline 26 (block 198), the spike in the pulmonary arterial pressure score and time span are logged in the combined measures set 95 (block 199). In the described embodiment, the mean arterial pressure on any spike in the arterial pressure tracing could be utilized.

(11) Exercise tolerance quality of life (QOL) measures (block 200): If the exercise tolerance QOL has decreased over 1.0 SD from the mean exercise tolerance in the reference baseline 26 (block 201), the decrease in exercise tolerance and the time span over which it occurs are logged in the combined measures set 95 (block 202).

(12) Respiratory distress quality of life (QOL) measures (block 203): If the respiratory distress QOL measure has deteriorated by more than 1.0 SD from the mean respiratory distress QOL measure in the reference baseline 26 (block 204), the increase in respiratory distress and the time span over which it occurs are logged in the combined measures set 95 (block 205).

(13) Spikes in right ventricular (RV) pressure (block 206): If short-lived spikes in the right ventricular pressure occur over time periods under 5 minutes compared to the reference baseline 26 (block 207), the spike in the right ventricular pressure and time span are logged in the combined measures set 95 (block 208).

(14) Spikes in transthoracic impedance (TTZ) (block 209): If short-lived spikes in the transthoracic impedance occur over time periods under 5 minutes compared to the reference baseline 26 (block 210), the spike in the transthoracic impedance and time span are logged in the combined measures set 95 (block 211).

(15) Atrial fibrillation (block 212): The presence or absence of atrial fibrillation (AF) is determined and, if present (block 213), atrial fibrillation is logged (block 214).

(16) Rhythm changes (block 215): The type and sequence of rhythm changes is significant and is determined (block 216) based on the timing of the relevant rhythm measure, such as sinus rhythm. For instance, a finding that a rhythm change to atrial fibrillation precipitated respiratory measures changes can indicate therapy directions against atrial fibrillation rather than the primary development of respiratory insufficiency. Thus, if there are rhythm changes (block 217), the sequence of the rhythm changes and time span are logged (block 211).

Note also that an inversion of the indicator thresholds 129 defined above could similarly be used for detecting a trend in disease regression. One skilled in the art would recognize that these measures would vary based on whether or not they were recorded during rest or during activity and that the measured activity score can be used to indicate the degree of patient rest or activity. The patient activity score can be determined via an implantable motion detector, for example, as described in U.S. Pat. No. 4,428,378, issued Jan. 31, 1984, to Anderson et al., the disclosure of which is incorporated herein by reference.

The indicator thresholds 129 for detecting a trend towards a state of respiratory insufficiency can also be used to declare, a priori, respiratory insufficiency present, regardless of preexisting trend data when certain limits are established, such as:

(1) An absolute limit of arterial oxygen (block 182) less than 85 mm Hg is an a priori definition of respiratory insufficiency from decreased oxygenation.

(2) An absolute limit of arterial carbon dioxide (block 185) falling below 25 mm Hg (in the absence of marked exercise) or greater than 50 mm Hg are both a priori definitions of respiratory insufficiency as indicated by hyperventilation and hypoventilation, respectively.

Figure 12:
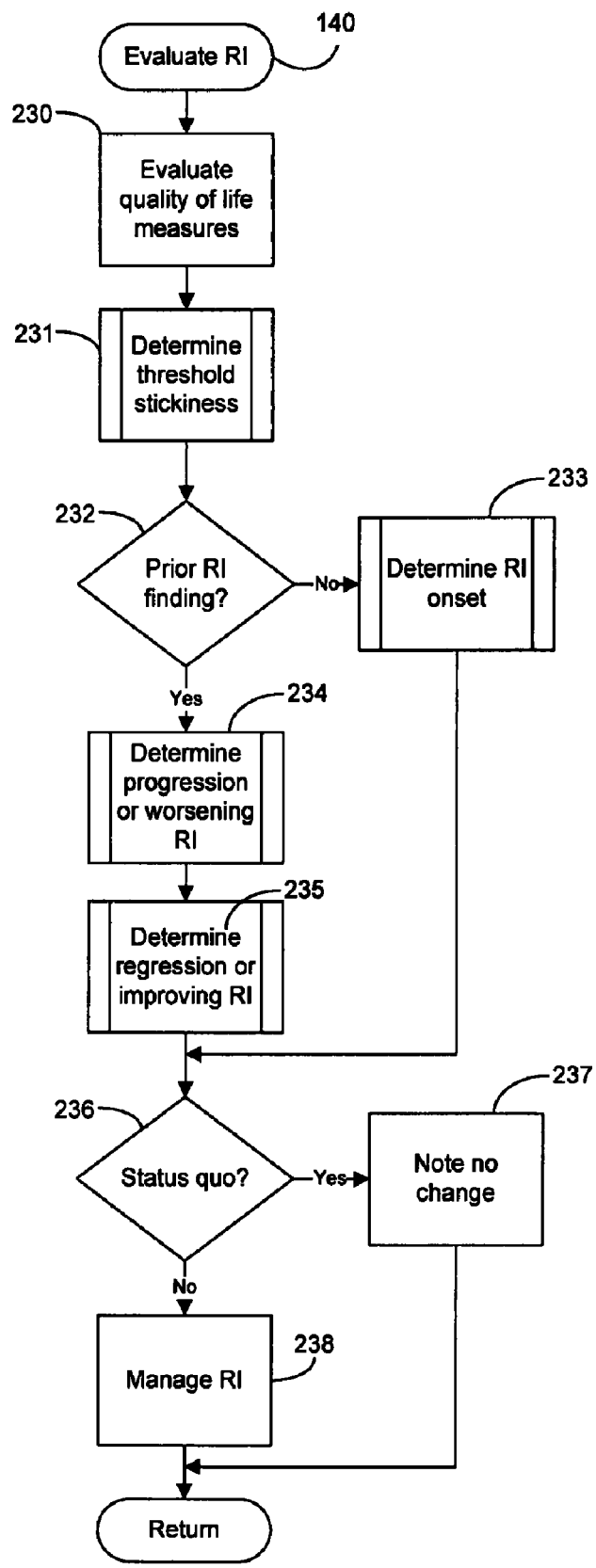
FIG. 12 is a flow diagram showing the routine for evaluating the onset, progression, regression, and status quo of respiratory insufficiency for use in the method of FIGS. 8A-8B.

FIG. 12 is a flow diagram showing the routine for evaluating the onset, progression, regression and status quo of respiratory insufficiency 140 for use in the method of FIGS. 8A and 8B. The purpose of this routine is to evaluate the presence of sufficient indicia to warrant a diagnosis of the onset, progression, regression, and status quo of respiratory insufficiency. Quality of life and symptom measures 25a, 25b can be included in the evaluation (block 230) by determining whether any of the individual quality of life and symptom measures 25a, 25b have changed relative to the previously collected quality of life and symptom measures from the monitoring sets 27 and the reference baseline 26, if used. For example, an increase in the shortness of breath measure 87 and exercise tolerance measure 92 would corroborate a finding of respiratory insufficiency. Similarly, a transition from NYHA Class II to NYHA Class III would indicate a deterioration or, conversely, a transition from NYHA Class III to NYHA Class II status would indicate improvement or progress when adapting the NYHA classifications for their parallel in lung disorders. Incorporating the quality of life and symptom measures 25a, 25b into the evaluation can help, in part, to refute or support findings based on physiological data. Next, a determination as to whether any changes to interventive measures are appropriate based on threshold stickiness ("hysteresis") is made (block 231), as further described below with reference to FIG. 16.

The routine returns upon either the determination of a finding or elimination of all factors as follows. If a finding of respiratory insufficiency was not previously diagnosed (block 232), a determination of disease onset is made (block 233), as further described below with reference to FIGS. 13A-13C. Otherwise, if respiratory insufficiency was previously diagnosed (block 232), a further determination of either disease progression or worsening (block 234) or regression or improving (block 235) is made, as further described below with reference to FIGS. 14A-14C and 15A-15C, respectively. If, upon evaluation, neither disease onset (block 233), worsening (block 234) or improving (block 235) is indicated, a finding of status quo is appropriate (block 236) and noted (block 237). Otherwise, respiratory insufficiency and the related outcomes are actively managed (block 238) through the administration of, non-exclusively, antibiotic and antiviral therapies, bronchodilator therapies, oxygen therapies, antiinflammation therapies, electrical therapies, mechanical therapies, and other therapies as are known in the art. The management of respiratory insufficiency is described, by way of example, in A. S. Fauci et al. (Eds.), "Harrison's Principles of Internal Medicine," pp. 1407-1491, McGraw-Hill, 14$^{th}$ Ed. (1997), the disclosure of which is incorporated herein by reference. The routine then returns.

Figure 13A:
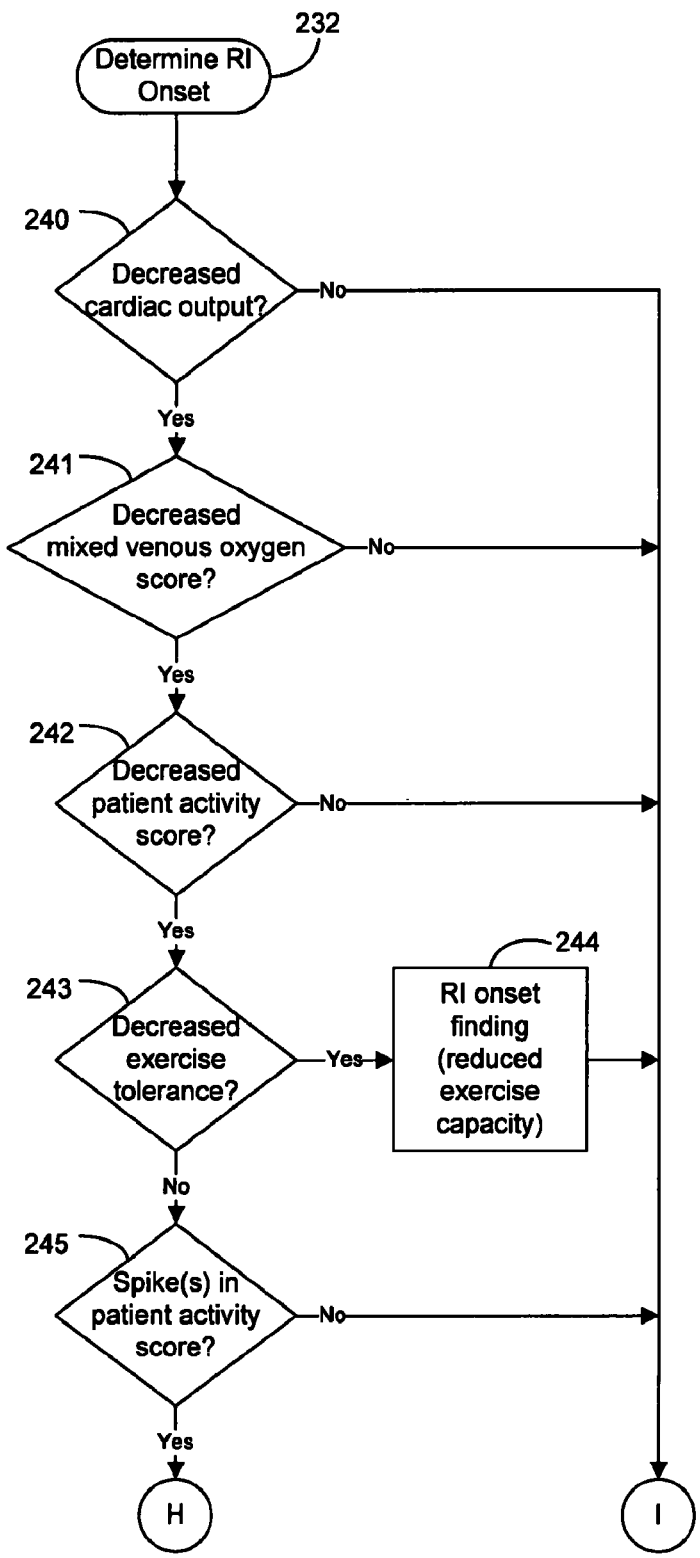
FIGS. 13A-13C are flow diagrams showing the routine for determining an onset of respiratory insufficiency for use in the routine of FIG. 12.
Figure 13B:
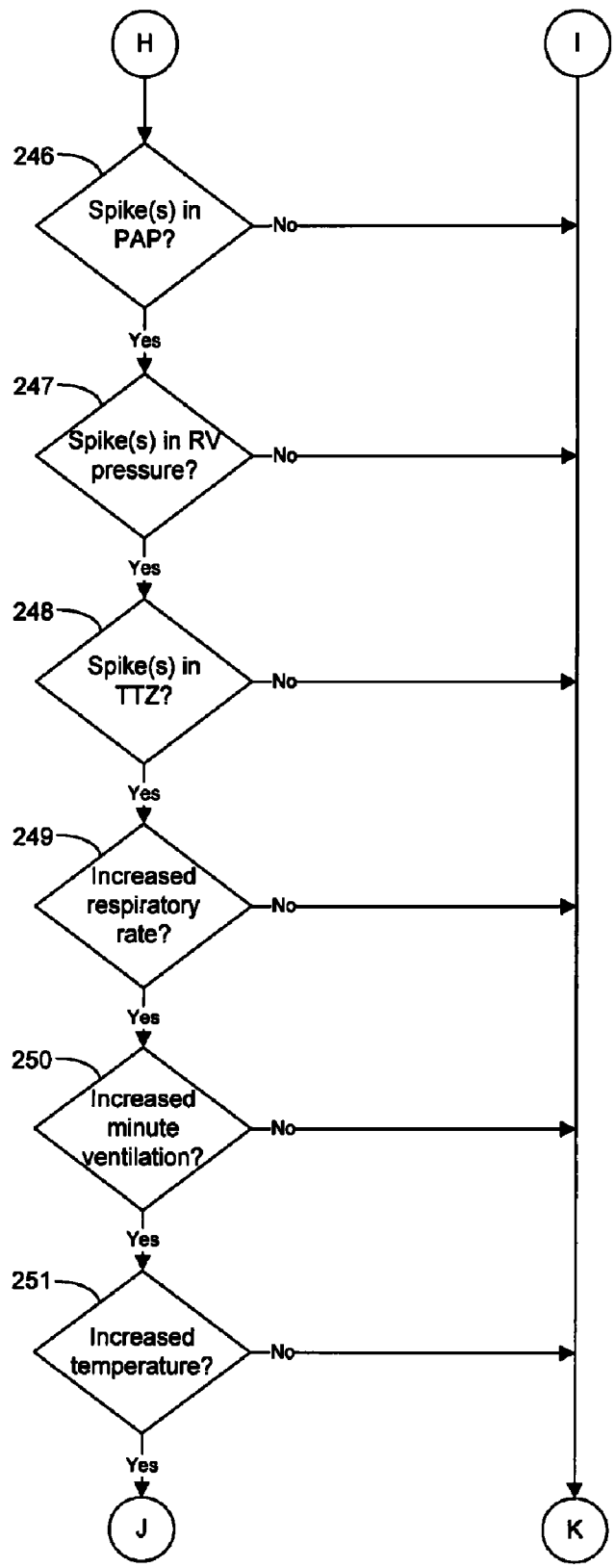
Figure 13C:
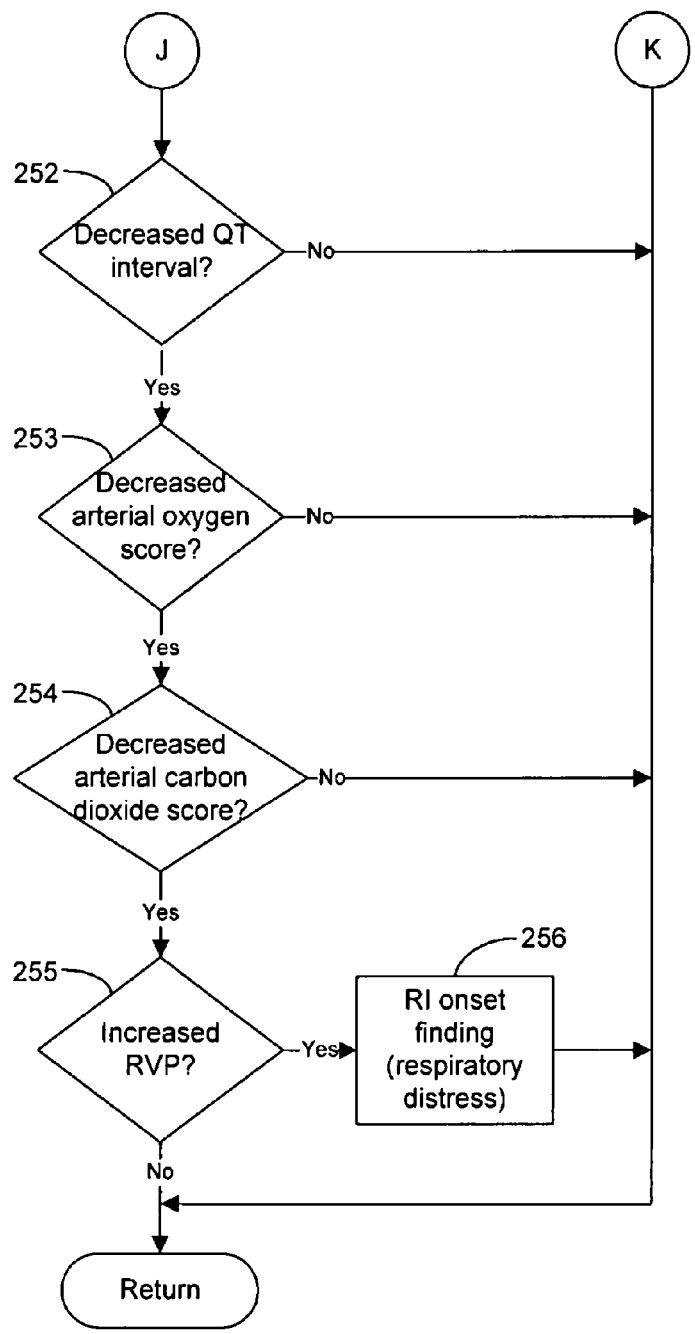

FIGS. 13A-13C are flow diagrams showing the routine for determining an onset of respiratory insufficiency 232 for use in the routine of FIG. 12. Respiratory insufficiency is possible based on two general symptom categories: reduced exercise capacity (block 244) and respiratory distress (block 256). An effort is made to diagnose respiratory insufficiency manifesting primarily as resulting in reduced exercise capacity (block 244) and/or increased respiratory distress (block 256). Reduced exercise capacity and respiratory distress can generally serve as markers of low systemic arterial oxygenation. The clinical aspects of respiratory insufficiency are described, by way of example, in A. S. Fauci et al. (Eds.), "Harrison's Principles of Internal Medicine," pp. 1410-1419, McGraw-Hill, 14$^{th}$ Ed. (1997), the disclosure of which is incorporated herein by reference.

As primary pulmonary disease considerations, multiple individual indications (blocks 240-243, 245-253) should be present for the two principal findings of respiratory insufficiency related reduced exercise capacity (block 244), or respiratory insufficiency related respiratory distress (block 256), to be indicated, both for disease onset or progression. The presence of primary key findings alone can be sufficient to indicate an onset of respiratory insufficiency and secondary key findings serve to corroborate disease onset. Note the presence of any abnormality can trigger an analysis for the presence or absence of secondary disease processes, such as the presence of atrial fibrillation or congestive heart failure. Secondary disease considerations can be evaluated using the same indications (see, e.g., blocks 141-144 of FIGS. 8A-8B), but with adjusted indicator thresholds 129 (shown in FIG. 5) triggered at a change of 0.5 SD, for example, instead of 1.0 SD.

In the described embodiment, the reduced exercise capacity and respiratory distress findings (blocks 244, 251) can be established by consolidating the individual indications (blocks 240-243, 245-253) in several ways. First, in a preferred embodiment, each individual indication (blocks 240-243, 245-253) is assigned a scaled index value correlating with the relative severity of the indication. For example, decreased cardiac output (block 240) could be measured on a scale from '1' to '5' wherein a score of '1' indicates no change in cardiac output from the reference point, a score of '2' indicates a change exceeding 0.5 SD, a score of '3' indicates a change exceeding 1.0 SD, a score of '4' indicates a change exceeding 2.0 SD, and a score of '5' indicates a change exceeding 3.0 SD. The index value for each of the individual indications (blocks 240-243, 245-253) can then either be aggregated or averaged with a result exceeding the aggregate or average maximum indicating an appropriate respiratory insufficiency finding.

Preferably, all scores are weighted depending upon the assignments made from the measures in the reference baseline 26. For instance, arterial partial pressure of oxygen 102 could be weighted more importantly than respiratory rate 104 if the respiratory rate in the reference baseline 26 is particularly high at the outset, making the detection of further disease progression from increases in respiratory rate, less sensitive. In the described embodiment, arterial partial pressure of oxygen 102 receives the most weight in determining a reduced exercise capacity finding whereas arterial partial pressure of carbon dioxide 107 receives the most weight in determining a respiratory distress or dyspnea finding.

Alternatively, a simple binary decision tree can be utilized wherein each of the individual indications (blocks 240-243, 245-253) is either present or is not present. All or a majority of the individual indications (blocks 240-243, 245-253) should be present for the relevant respiratory insufficiency finding to be affirmed.

Other forms of consolidating the individual indications (blocks 240-243, 245-253) are feasible.

Figure 14A:
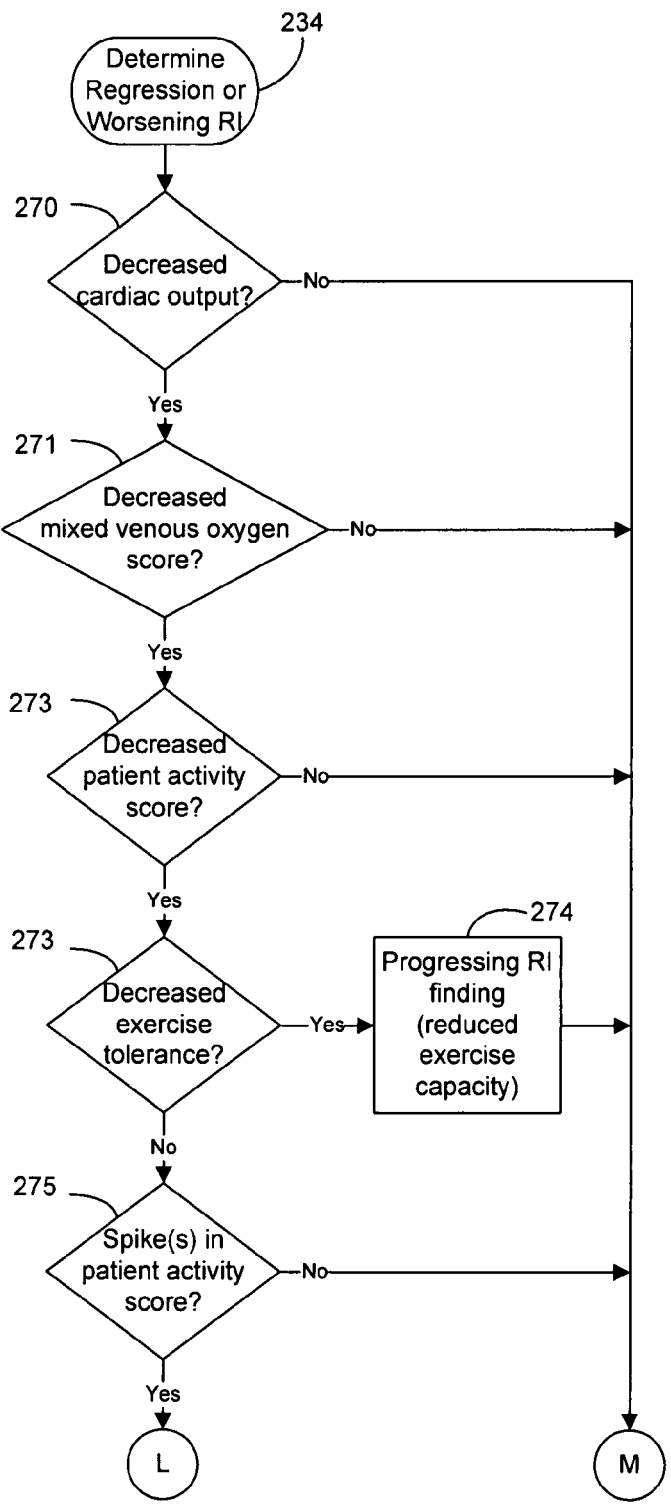
FIGS. 14A-14C are flow diagrams showing the routine for determining progression or worsening of respiratory insufficiency for use in the routine of FIG. 12.
Figure 14B:
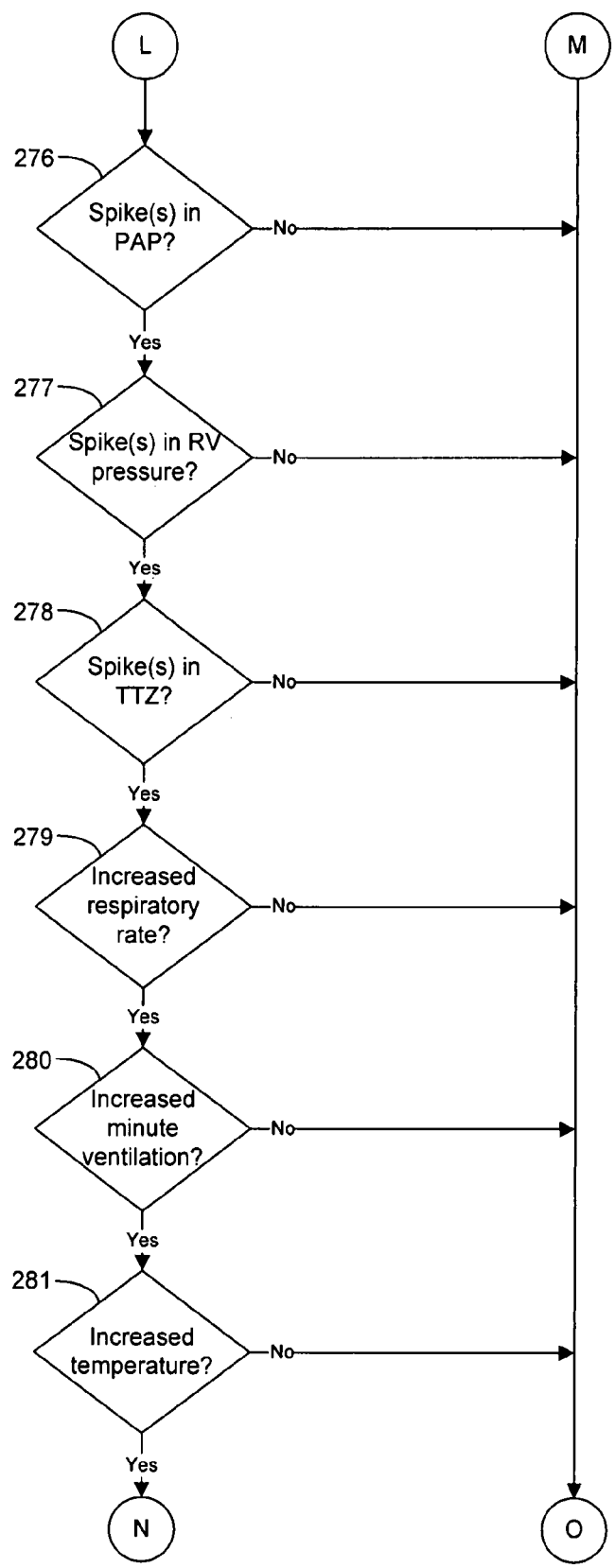
Figure 14C:
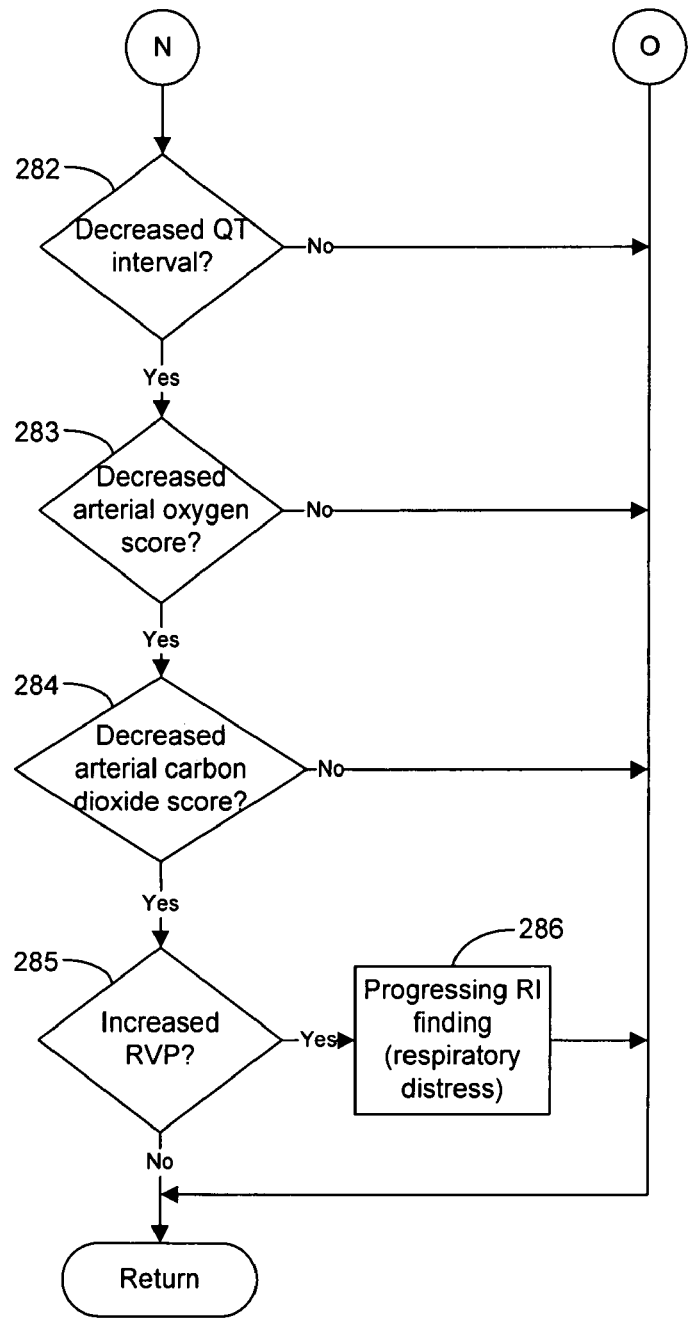

FIGS. 14A-14C are flow diagrams showing the routine for determining a progression or worsening of respiratory insufficiency 234 for use in the routine of FIG. 12. The primary difference between the determinations of disease onset, as described with reference to FIGS. 13A-13C, and disease progression is the evaluation of changes indicated in the same factors present in a disease onset finding. Thus, a revised respiratory insufficiency finding is possible based on the same two general symptom categories: reduced exercise capacity (block 274) and respiratory distress (block 286). The same factors which need be indicated to warrant a diagnosis of respiratory insufficiency onset are evaluated to determine disease progression.

Figure 15A:
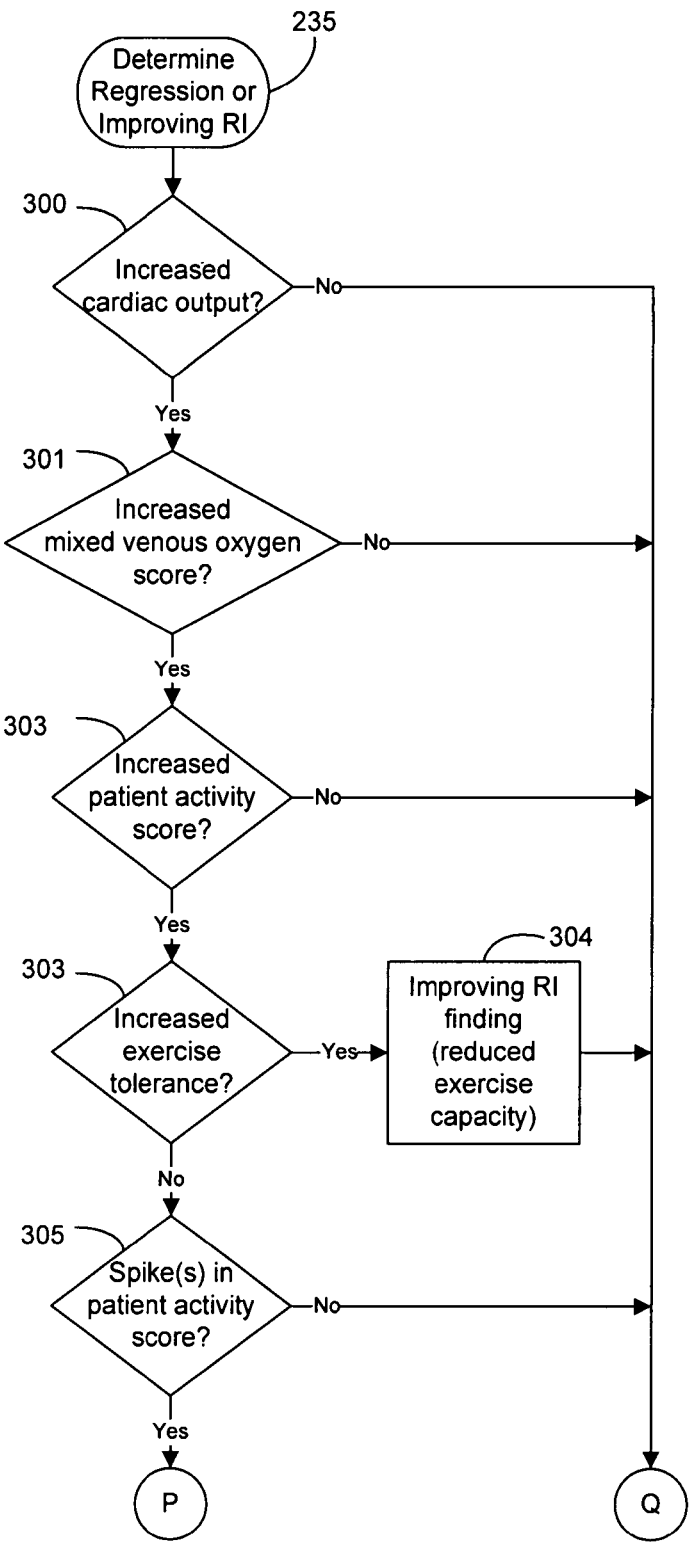
FIGS. 15A-15C are flow diagrams showing the routine for determining regression or improving of respiratory insufficiency for use in the routine of FIG. 12.
Figure 15B:
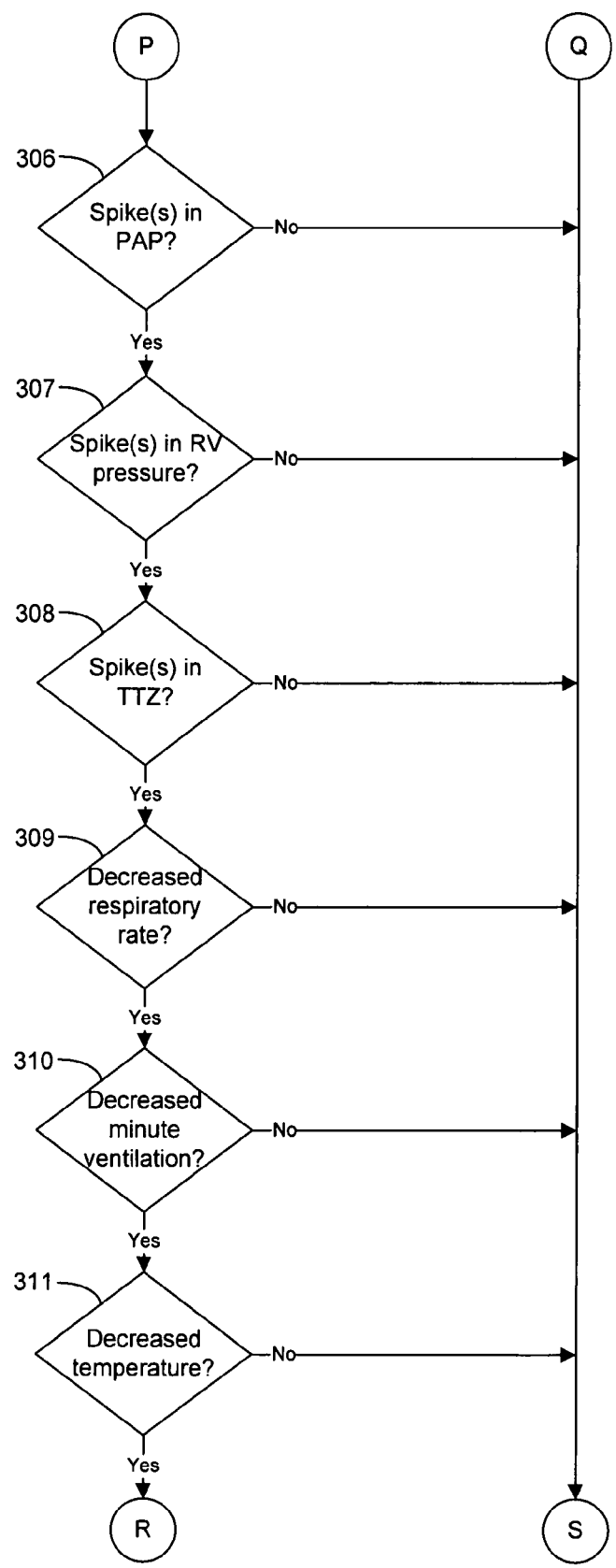
Figure 15C:
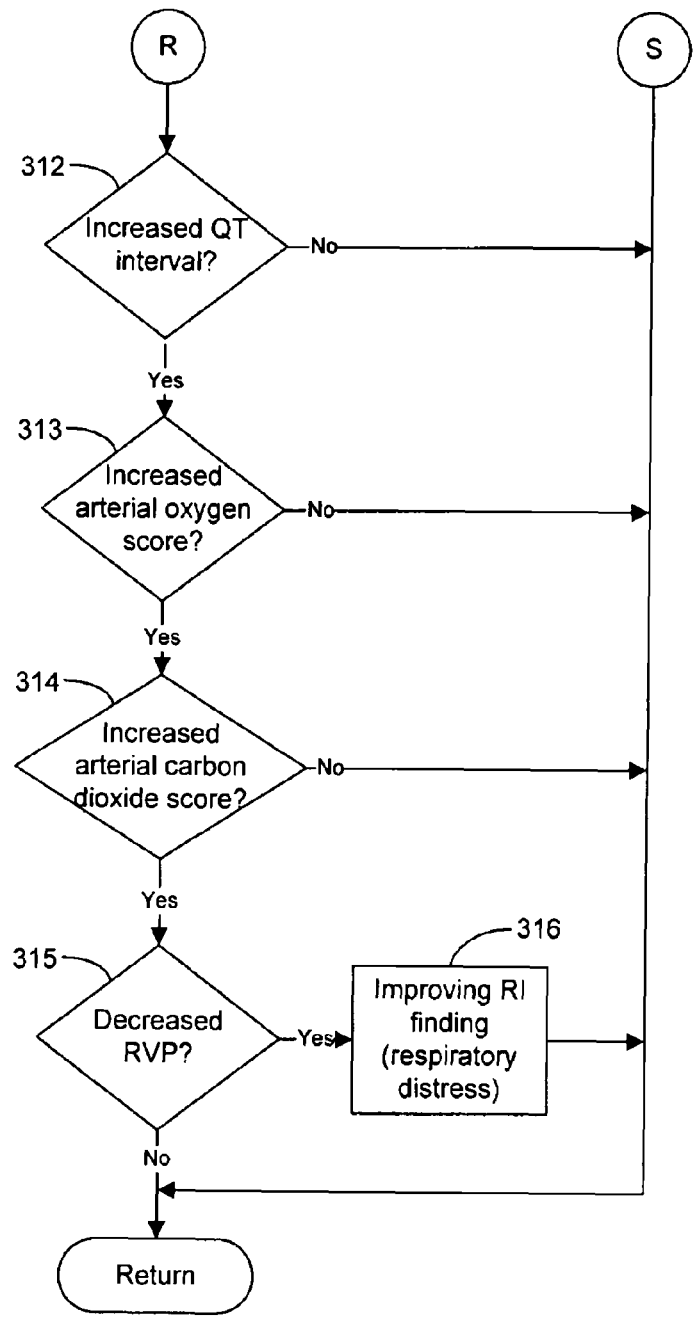

Similarly, FIGS. 15A-15C are flow diagrams showing the routine for determining a regression or improving of respiratory distress 235 for use in the routine of FIG. 12. The same factors as described above with reference to FIGS. 13A-13C and 14A-14C, trending in opposite directions from disease onset or progression, are evaluated to determine disease regression. As primary cardiac disease considerations, multiple individual indications (blocks 300-303, 305-313) should be present for the two principal findings of respiratory insufficiency related reduced exercise capacity (block 304), or respiratory insufficiency related respiratory distress (block 316), to indicate disease regression.

Figure 16:
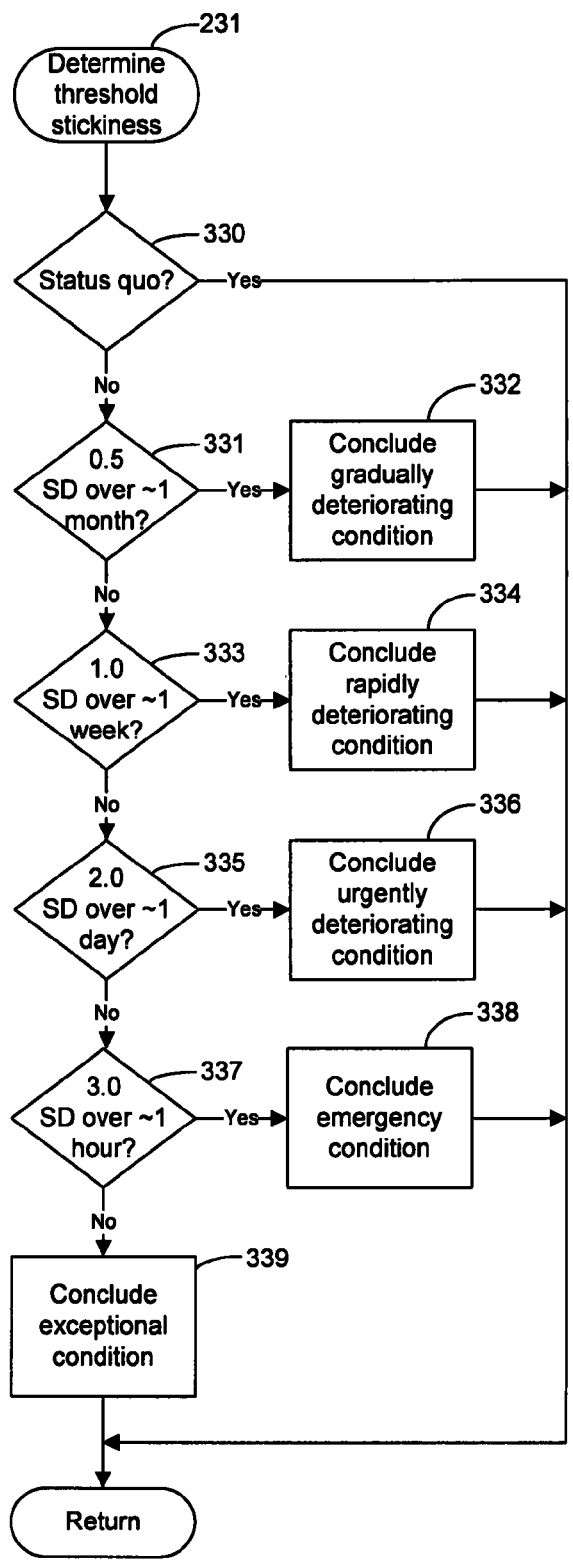
FIG. 16 is a flow diagram showing the routine for determining threshold stickiness ("hysteresis") for use in the method of FIG. 12.

FIG. 16 is a flow diagram showing the routine for determining threshold stickiness ("hysteresis") 231 for use in the method of FIG. 12. Stickiness, also known as hysteresis, is a medical practice doctrine whereby a diagnosis or therapy will not be changed based upon small or temporary changes in a patient reading, even though those changes might temporarily move into a new zone of concern. For example, if a patient measure can vary along a scale of '1' to '10' with '10' being worse, a transient reading of '6,' standing alone, on a patient who has consistently indicated a reading of '5' for weeks will not warrant a change in diagnosis without a definitive prolonged deterioration first being indicated. Stickiness dictates that small or temporary changes require more diagnostic certainty, as confirmed by the persistence of the changes, than large changes would require for any of the monitored (device) measures. Stickiness also makes reversal of important diagnostic decisions, particularly those regarding life-threatening disorders, more difficult than reversal of diagnoses of modest import. As an example, automatic external defibrillators (AEDs) manufactured by Heartstream, a subsidiary of Agilent Technologies, Seattle, Wash., monitor heart rhythms and provide interventive shock treatment for the diagnosis of ventricular fibrillation. Once diagnosis of ventricular fibrillation and a decision to shock the patient has been made, a pattern of no ventricular fibrillation must be indicated for a relatively prolonged period before the AED changes to a "no-shock" decision. As implemented in this AED example, stickiness mandates certainty before a decision to shock is disregarded. In practice, stickiness also dictates that acute deteriorations in disease state are treated aggressively while chronic, more slowly progressing disease states are treated in a more tempered fashion. However, in the case of some of the parameters being followed, such as activity and pulmonary artery systolic pressure, abrupt spikes in these measures can be indicative of coughing and therefore helpful in indicating the onset of a disorder that might lead to pulmonary insufficiency.

Thus, if the patient status indicates a status quo (block 330), no changes in treatment or diagnosis are indicated and the routine returns. Otherwise, if the patient status indicates a change away from status quo (block 330), the relative quantum of change and the length of time over which the change has occurred is determinative. If the change of approximately 0.5 SD has occurred over the course of about one month (block 331), a gradually deteriorating condition exists (block 332) and a very tempered diagnostic, and if appropriate, treatment program is undertaken. If the change of approximately 1.0 SD has occurred over the course of about one week (block 333), a more rapidly deteriorating condition exists (block 334) and a slightly more aggressive diagnostic, and if appropriate, treatment program is undertaken. If the change of approximately 2.0 SD has occurred over the course of about one day (block 335), an urgently deteriorating condition exists (block 336) and a moderately aggressive diagnostic, and if appropriate, treatment program is undertaken. If the change of approximately 3.0 SD has occurred over the course of about one hour (block 337), an emergency condition exists (block 338) and an immediate diagnostic, and if appropriate, treatment program is undertaken as is practical. Finally, if the change and duration fall outside the aforementioned ranges (blocks 331-338), an exceptional condition exists (block 339) and the changes are reviewed manually, if necessary. The routine then returns. These threshold limits and time ranges may then be adapted depending upon patient history and peer-group guidelines.

The present invention provides several benefits. One benefit is improved predictive accuracy from the outset of patient care when a reference baseline is incorporated into the automated diagnosis. Another benefit is an expanded knowledge base created by expanding the methodologies applied to a single patient to include patient peer groups and the overall patient population. Collaterally, the information maintained in the database could also be utilized for the development of further predictive techniques and for medical research purposes. Yet a further benefit is the ability to hone and improve the predictive techniques employed through a continual reassessment of patient therapy outcomes and morbidity rates.

Other benefits include an automated, expert system approach to the cross-referral, consideration, and potential finding or elimination of other diseases and health disorders with similar or related etiological indicators and for those other disorders that may have an impact on respiratory insufficiency. Although disease specific markers will prove very useful in discriminating the underlying cause of symptoms, many diseases, other than respiratory insufficiency, will alter some of the same physiological measures indicative of respiratory insufficiency. Consequently, an important aspect of considering the potential impact of other disorders will be, not only the monitoring of disease specific markers, but the sequencing of change and the temporal evolution of more general physiological measures, for example respiratory rate, pulmonary artery diastolic pressure, and cardiac output, to reflect disease onset, progression or regression in more than one type of disease process, especially congestive heart failure from whatever cause.

While the invention has been particularly shown and described as referenced to the embodiments thereof, those skilled in the art will understand that the foregoing and other changes in form and detail may be made therein without departing from the spirit and scope of the invention.

What is claimed is:

1. An automated collection and analysis patient care system for diagnosing and monitoring respiratory insufficiency and outcomes thereof, comprising:

a database storing patient monitoring information, comprising:
  a plurality of monitoring sets, each monitoring set comprising recorded measures which each relate to patient information and comprise either medical device measures or derived measures calculable therefrom, the medical device measures having been recorded on a substantially continuous basis;
  a set of stored indicator thresholds, each indicator threshold corresponding to a quantifiable physiological measure of a pathophysiology indicative of respiratory insufficiency and relating to a same type of patient information as at least one of the recorded measures, the database further storing a reference baseline comprising recorded measures which each relate to patient information recorded by the medical device adapted to be implanted during an initial time period and comprise either device measures recorded by the medical device adapted to be implanted or derived measures calculable therefrom, and recorded measures relating to patient information for one of the individual patients solely, a peer group of patients to which the individual patient belongs, and a general population of patients;
a server diagnosing a respiratory insufficiency finding, comprising:
  an analysis module determining a change in patient wellness by comparing at least one recorded measure to at least one other recorded measure with both recorded measures relating to the same type of patient information; and
  a comparison module comparing each patient wellness change to at least one of the stored indicator thresholds corresponding to the same type of patient information as the recorded measures which were compared; and
  a database module obtaining at least one of the at least one recorded measure and the at least one other recorded measure from the retrieved reference baseline.

2. A system according to claim 1, wherein the device measures are recorded by at least one of a medical device adapted to be implanted in an individual patient and an external medical device proximal to the individual patient when the device measures are recorded.

3. A system according to claim 1, wherein each of the monitoring sets comprises recorded measures relating to patient information solely for the individual patient, further comprising:
  the database module further retrieving each monitoring set from a patient care record for the individual patient and obtaining the at least one recorded measure and the at least one other recorded measure from the retrieved monitoring sets.

4. A system according to claim 1, wherein each of the monitoring sets comprises recorded measures relating to patient information for a peer group of patients to which the individual patient belongs, further comprising:
  the database module further retrieving at least one monitoring set from a patient care record for the individual patient, retrieving at least one other monitoring set from a patient care record in the same patient peer group, and obtaining the at least one recorded measure from the at least one monitoring set and the at least one other recorded measure from the at least one other monitoring set.

5. A system according to claim 1, wherein each of the monitoring sets comprises recorded measures relating to patient information for the general population of patients, further comprising:
  the database module retrieving at least one monitoring set from a patient care record for the individual patient, retrieving at least one other monitoring set from a patient care record in the overall patient population, and obtaining the at least one recorded measure from the at least one monitoring set and the at least one other recorded measure from the at least one other monitoring set.

6. A system according to claim 1, wherein the indicator thresholds relate to at least one of reduced exercise capacity selected from the group comprising decreased cardiac output, decreased mixed venous oxygen score, decreased patient activity score and decreased exercise tolerance and respiratory distress selected from the group comprising a spike in patient activity score, a spike in pulmonary artery pressure, a spike in right ventricular pressure, a spike in transthoracic impedance, increased respiratory rate, increased minute ventilation, increased temperature, decreased QT interval, decreased arterial oxygen and decreased arterial carbon dioxide.

7. A system according to claim 1, the comparison module further comprising at least one of:
  a graded comparison module to perform a graded comparison, comprising:
    a submodule grading the comparisons between each patient wellness change and corresponding indicator threshold on a fixed scale based on a degree of deviation from the indicator threshold; and
    the comparison module determining an overall patient wellness change by performing a summation over individual graded comparisons; and
  a weighted comparison module to perform a weighted comparison, comprising:
    a submodule determining probabilistic weightings of the comparisons between each patient wellness change and corresponding indicator threshold based on a statistical deviation and trends via linear fits from the indicator threshold; and
    the comparison module determining an overall patient wellness change by performing a summation over individual weightings of the comparisons.

8. A system according to claim 1, wherein each monitoring set further comprises quality of life and symptom measures recorded by the individual patient, the server further comprising:
  a quality of life module determining a change in patient wellness by comparing at least one recorded quality of life measure to at least one other corresponding recorded quality of life measure; and
  the server incorporating each patient wellness change in quality of life into the respiratory insufficiency finding to either refute or support a diagnosis.

9. A system according to claim 1, further comprising:
  a set of stored further indicator thresholds, each indicator threshold corresponding to a quantifiable physiological measure used to detect a pathophysiology indicative of diseases other than respiratory insufficiency; and
  the server diagnosing a finding of a disease other than respiratory insufficiency, the comparison module further comprising comparing each patient wellness change to each such further indicator threshold corresponding to the same type of patient information as the at least one recorded measure and the at least one other recorded measure.

10. A system according to claim 1, further comprising:
a set of stickiness indicators, each stickiness indicator corresponding to a temporal limit related to a course of patient care; and
a feedback module comparing a time span between each patient wellness change for each recorded measure to one of the set of stickiness indicators corresponding to the same type of patient information as the recorded measure being compared.

11. A system according to claim 1, further comprising:
a feedback module performing an interactive dialogue between the individual patient and the patient care system regarding a medical condition of the individual patient and providing automated feedback to the individual patient when a respiratory insufficiency finding is indicated.

12. A method for diagnosing and monitoring respiratory insufficiency using an automated collection and analysis patient care system, comprising:
storing a plurality of monitoring sets into a database, each monitoring set comprising recorded measures which each relate to patient information and comprise either medical device measures or derived measures calculable therefrom, the medical device measures having been recorded on a substantially continuous basis;
retrieving the plurality of monitoring sets from the database;
defining a set of indicator thresholds, each indicator threshold corresponding to a quantifiable physiological measure of a pathophysiology indicative of respiratory insufficiency and relating to a same type of patient information as at least one of the recorded measures; and
diagnosing a respiratory insufficiency finding, comprising:
determining a change in patient wellness by comparing at least one recorded measure to at least one other recorded measure with both recorded measures relating to the same type of patient information;
comparing each patient wellness change to one of the indicator thresholds corresponding to the same type of patient information as the recorded measures which were compared; and
retrieving a reference baseline comprising recorded measures which each relate to patient information recorded by the medical device adapted to be implanted during an initial time period and comprise either device measures recorded by the medical device adapted to be implanted or derived measures calculable therefrom; and
obtaining at least one of the at least one recorded measure and the at least one other recorded measure from the retrieved reference baseline.

13. A method according to claim 12, recording the device measures by at least one of a medical device adapted to be implanted in an individual patient and an external medical device proximal to the individual patient when the device measures are recorded.

14. A method according to claim 12, wherein each of the monitoring sets comprises recorded measures relating to patient information solely for an individual patient, further comprising:
retrieving each monitoring set from a patient care record for an individual patient; and
obtaining the at least one recorded measure and the at least one other recorded measure from the retrieved monitoring sets.

15. A method according to claim 12, wherein each of the monitoring sets comprises recorded measures relating to patient information for a peer group of patients to which an individual patient belongs, further comprising:
retrieving at least one monitoring set from a patient care record for an individual patient;
retrieving at least one other monitoring set from a patient care record in a same patient peer group; and
obtaining the at least one recorded measure from the at least one monitoring set and the at least one other recorded measure from the at least one other monitoring set.

16. A method according to claim 12, wherein each of the monitoring sets comprises recorded measures relating to patient information for a general population of patients, further comprising:
retrieving at least one monitoring set from a patient care record for an individual patient;
retrieving at least one other monitoring set from a patient care record in an overall patient population; and
obtaining the at least one recorded measure from the at least one monitoring set and the at least one other recorded measure from the at least one other monitoring set.

17. A method according to claim 12, wherein the reference baseline comprises recorded measures relating to patient information for one of the individual patients solely, a peer group of patients to which the individual patient belongs, and a general population of patients.

18. A method according to claim 12, wherein the indicator thresholds relate to at least one of reduced exercise capacity selected from the group comprising decreased cardiac output, decreased mixed venous oxygen score, decreased patient activity score and decreased exercise tolerance and respiratory distress selected from the group comprising a spike in patient activity score, a spike in pulmonary artery pressure, a spike in right ventricular pressure, a spike in transthoracic impedance, increased respiratory rate, increased minute ventilation, increased temperature, decreased QT interval, decreased arterial oxygen and decreased arterial carbon dioxide.

19. A method according to claim 12, the operation of comparing each patient wellness change further comprising at least one of:
performing a graded comparison, comprising:
grading the comparisons between each patient wellness change and corresponding indicator threshold on a fixed scale based on a degree of deviation from the indicator threshold to form individual graded comparisons; and
determining an overall patient wellness change by performing a summation over the individual graded comparisons; and
performing a weighted comparison, comprising:
determining probabilistic individual weightings of the comparisons between each patient wellness change and the corresponding indicator threshold based on a statistical deviation and trends via linear fits from the indicator threshold; and
determining an overall patient wellness change by performing a summation over the individual weightings of the comparisons.

20. A method according to claim 12, wherein each monitoring set further comprises quality of life and symptom measures recorded by an individual patient, diagnosing a respiratory insufficiency finding further comprising:

determining a change in patient wellness by comparing at least one recorded quality of life measure to at least one other corresponding recorded quality of life measure; and incorporating each patient wellness change in quality of life into the respiratory insufficiency finding to either refute or support the diagnosis.

21. A method according to claim 12, further comprising:
defining a set of further indicator thresholds, each indicator threshold corresponding to a quantifiable physiological measure used to detect a pathophysiology indicative of diseases other than respiratory insufficiency; and
diagnosing a finding of a disease other than respiratory insufficiency, comprising comparing each patient wellness change to each such further indicator threshold corresponding to the same type of patient information as the at least one recorded measure and the at least one other recorded measure.

22. A method according to claim 12, further comprising:
defining a set of stickiness indicators, each stickiness indicator corresponding to a temporal limit related to a course of patient care; and
comparing a time span between each patient wellness change for each recorded measure to one of the stickiness indicators corresponding to the same type of patient information as the recorded measure being compared.

23. A method according to claim 12, further comprising:
performing an interactive dialogue between an individual patient and the patient care system regarding a medical condition of the individual patient; and
providing automated feedback to the individual patient when a respiratory insufficiency finding is indicated.

24. A computer-readable storage medium holding code for diagnosing and monitoring respiratory insufficiency using an automated collection and analysis patient care system, comprising:
code for storing a plurality of monitoring sets into a database, each monitoring set comprising recorded measures which each relate to patient information and comprise either medical device measures or derived measures calculable therefrom, the medical device measures having been recorded on a substantially continuous basis;
code for retrieving the plurality of monitoring sets from the database;
code for defining a set of indicator thresholds, each indicator threshold corresponding to a quantifiable physiological measure of a pathophysiology indicative of respiratory insufficiency and relating to a same type of patient information as at least one of the recorded measures; and
code for diagnosing a respiratory insufficiency finding, comprising:
code for determining a change in patient wellness by comparing at least one recorded measure to at least one other recorded measure with both recorded measures relating to the same type of patient information; and
code for comparing each patient wellness change to an indicator threshold corresponding to the same type of patient information as the recorded measures which were compared, wherein comparing each patient wellness change further comprises at least one of:
code for performing a graded comparison, comprising:
code for grading the comparisons between each patient wellness change and corresponding indicator threshold on a fixed scale based on a degree of deviation from the indicator threshold to form individual graded comparisons; and
code for determining an overall patient wellness change by performing a summation over the individual graded comparisons; and
code for performing a weighted comparison, comprising:
code for determining probabilistic individual weightings of the comparisons between each patient wellness change and the corresponding indicator threshold based on a statistical deviation and trends via linear fits from the corresponding indicator threshold; and
code for determining an overall patient wellness change by performing a summation over the individual weightings of the comparisons.

25. A storage medium according to claim 24, wherein each of the monitoring sets comprises recorded measures relating to patient information solely for an individual patient, further comprising:
code for retrieving each monitoring set from a patient care record for an individual patient; and
code for obtaining the at least one recorded measure and the at least one other recorded measure from the retrieved monitoring set.

26. A storage medium according to claim 24, wherein each of the monitoring sets comprises recorded measures relating to patient information for a peer group of patients to which an individual patient belongs, further comprising:
code for retrieving at least one monitoring set from a patient care record for an individual patient;
code for retrieving at least one other monitoring set from a patient care record in the same patient peer group; and
code for obtaining the at least one recorded measure from the at least one monitoring set and the at least one other recorded measure from the at least one other monitoring set.

27. A storage medium according to claim 24, wherein each of the monitoring sets comprises recorded measures relating to patient information for a general population of patients, further comprising:
code for retrieving at least one monitoring set from a patient care record for an individual patient;
code for retrieving at least one other monitoring set from a patient care record in an overall patient population; and
code for obtaining the at least one recorded measure from the at least one monitoring set and the at least one other recorded measure from the at least one other monitoring set.

28. A storage medium according to claim 24, further comprising:
code for retrieving a reference baseline comprising recorded measures which each relate to patient information recorded by the medical device adapted to be implanted during an initial time period and comprise either device measures recorded by the medical device adapted to be implanted or derived measures calculable therefrom; and
code for obtaining at least one of the at least one recorded measure and the at least one other recorded measure from the retrieved reference baseline.

29. A storage medium according to claim 24, wherein each monitoring set further comprises quality of life and symptom measures recorded by an individual patient, the operation of diagnosing a respiratory insufficiency finding further comprising:

code for determining a change in patient wellness by comparing at least one recorded quality of life measure to at least one other corresponding recorded quality of life measure; and code for incorporating each patient wellness change in quality of life into the respiratory insufficiency finding to either refute or support the diagnosis.

30. A storage medium according to claim 24, further comprising:

code for defining a set of further indicator thresholds, each indicator threshold corresponding to a quantifiable physiological measure used to detect a pathophysiology indicative of diseases other than respiratory insufficiency; and code for diagnosing a finding of a disease other than respiratory insufficiency, comprising comparing each patient wellness change to each such further indicator threshold corresponding to the same type of patient information as the at least one recorded measure and the at least one other recorded measure.

31. A storage medium according to claim 24, further comprising:

code for defining a set of stickiness indicators, each stickiness indicator corresponding to a temporal limit related to a course of patient care; and code for comparing a time span between each patient wellness change for each recorded measure to a stickiness indicator corresponding to the same type of patient information as the recorded measure being compared.

32. A storage medium according to claim 24, further comprising:

code for performing an interactive dialogue between the individual patient and the patient care system regarding a medical condition of an individual patient; and code for providing automated feedback to the individual patient when a respiratory insufficiency finding is indicated.

* * * * *